US008932808B1

(12) United States Patent
Sarwal et al.

(10) Patent No.: US 8,932,808 B1
(45) Date of Patent: Jan. 13, 2015

(54) METHODS AND COMPOSITIONS FOR DETERMINING A GRAFT TOLERANT PHENOTYPE IN A SUBJECT

(75) Inventors: Minnie M. Sarwal, Portola Valley, CA (US); Elaine Mansfield, Sunnyvale, CA (US); Sophie Brouard, Nantes (FR); Jean-Paul Soulillou, Nantes (FR)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 652 days.

(21) Appl. No.: 10/585,610

(22) PCT Filed: Jan. 20, 2005

(86) PCT No.: PCT/US2005/004799
§ 371 (c)(1),
(2), (4) Date: May 31, 2007

(87) PCT Pub. No.: WO2005/070086
PCT Pub. Date: Aug. 4, 2005

Related U.S. Application Data

(60) Provisional application No. 60/538,439, filed on Jan. 21, 2004, provisional application No. 60/571,471, filed on May 14, 2004.

(51) Int. Cl.
*C12Q 1/68* (2006.01)
*C12P 19/34* (2006.01)
*C07H 21/02* (2006.01)

(52) U.S. Cl.
USPC ..... 435/6.1; 435/91.2; 435/287.2; 435/287.1; 536/23.1

(58) Field of Classification Search
CPC .................. C12Q 2600/158; C12Q 2600/118; G01N 2800/245; G01N 2800/347
See application file for complete search history.

(56) References Cited

U.S. PATENT DOCUMENTS

| | | | |
|---|---|---|---|
| 6,607,879 B1 | 8/2003 | Cocks et al. | |
| 7,026,121 B1 | 4/2006 | Wohlgemuth et al. | |
| 7,879,556 B2 | 2/2011 | Wohlgemuth et al. | |
| 2003/0017619 A1 | 1/2003 | Rokubo et al. | |
| 2003/0104371 A1 | 6/2003 | Strom et al. | |
| 2004/0163654 A1 | 8/2004 | Williams | |
| 2006/0088836 A1 | 4/2006 | Wohlgemuth et al. | |
| 2006/0088876 A1 | 4/2006 | Bauer | |
| 2006/0246485 A1* | 11/2006 | Sarwal et al. ............ 435/6 |
| 2006/0269949 A1 | 11/2006 | Halloran et al. | |
| 2006/0281122 A1 | 12/2006 | Bryant et al. | |
| 2007/0031890 A1 | 2/2007 | Wohlgemuth et al. | |
| 2007/0111210 A1 | 5/2007 | Bigaud et al. | |
| 2007/0122806 A1 | 5/2007 | Strom et al. | |
| 2007/0134728 A1 | 6/2007 | Hu et al. | |
| 2007/0212701 A1 | 9/2007 | O'Toole et al. | |
| 2007/0232658 A1 | 10/2007 | Wagner et al. | |
| 2007/0264272 A1 | 11/2007 | Perreault et al. | |
| 2008/0233573 A1 | 9/2008 | Storm et al. | |
| 2009/0022730 A1 | 1/2009 | Raulf et al. | |
| 2009/0197286 A1 | 8/2009 | Karin et al. | |
| 2009/0269334 A1 | 10/2009 | Bigaud et al. | |
| 2009/0304705 A1 | 12/2009 | Grass | |
| 2010/0120629 A1 | 5/2010 | Ellis et al. | |
| 2011/0201519 A1 | 8/2011 | Sarwal et al. | |
| 2013/0157888 A1 | 6/2013 | Nagele | |

FOREIGN PATENT DOCUMENTS

| | | |
|---|---|---|
| EP | 1731620 | 12/2006 |
| EP | 2295966 | 3/2011 |
| WO | 2004/074815 | 9/2004 |
| WO | 2007/104537 | 9/2007 |
| WO | 2007/121922 | 11/2007 |
| WO | 2008/009132 | 1/2008 |
| WO | 2008/084331 | 7/2008 |
| WO | 2009/143624 | 12/2009 |
| WO | 2010038974 | 8/2010 |

OTHER PUBLICATIONS

Enard W. et al. Science (Apr. 12, 2002) vol. 296 pp. 340-343.*
Flechner S.M. et al American Journal of Transplantation (2004) vol. 4, pp. 1475-1489.*
Cheung V.G. et al. Nature Genetics (Mar. 2003) vol. 33, pp. 422-425.*
Chan E. Drug Discovery and Development (Apr. 1, 2006), printed from www.ddmag.com, printed pp. 1-6.*
Martinez-Llordella M. et al. The Journal of Clinical Investigations (Aug. 2008) vol. 118 No. 8, pp. 2845-2857.*
Chu T.W. et al. Genomics (1995) vol. 29 pp. 229-239.*

(Continued)

*Primary Examiner* — Stephen Kapushoc
(74) *Attorney, Agent, or Firm* — Bozicevic, Field & Francis LLP; Bret E. Field; Kyle A. Gurley

(57) ABSTRACT

Methods are provided for determining whether a subject has a graft tolerant phenotype. In practicing the subject methods, the expression of at least one gene in a sample from the subject, e.g., a blood sample, is assayed to obtain an expression evaluation for the at least one gene. The obtained expression evaluation is then employed to determine whether the subject has a graft tolerant phenotype. Also provides are compositions, systems and kits that find use in practicing the subject methods. The methods and compositions find use in a variety of applications, including the determination of an immunosuppressive therapy regimen.

12 Claims, 8 Drawing Sheets

(56) References Cited

OTHER PUBLICATIONS

Chen G. et al "Discordant Protein and mRNA Expression in Lung Adenocarcinomas" Molecular and Cellualr Proteomics 1.4 (2002) pp. 304-313.*

Zhang H.Q. et al. Transplantation Proceedings, 34, 1757-1759 (2002).*

Wakui et al. "Genes Highly Expressed in the Early Phase of Murine Graft-Versus-Host Reaction," Biochemical and Biophysical Communications (2001) 282:200-206.

Simon et al. "Serial Peripheral Blood Perforin and Granzyme B Gene Expression Measurements for Prediction of Acute Rejection in Kidney Graft Recipients," American Journal of Transplantation (2003) 3:1121-1127.

Chua et al. "Application of Microarrays to Renal Transplantation: Progress and Possibilities," Frontiers in Bioscience (2003) 8:s913-923.

Wu "Analysing Gene Expression Data From DNA Microarrays to Identify Candidate Genes," Journal of Pathology (2001) 195:53-65.

Cheung et al. "Natural Variation in Human Gene Expression Assessed in Lymphoblastoid Cells," Nature Genetics (2003) 33:422-425.

Medbury et al. "The Cytokine and Histological Response in Islet Xenograft Rejection is Dependent Upon Species Combination," Transplantation (1997) 64(9):1307-1314.

Sarwal, Minnie; et al., "Molecular Heterogeneity in Acute Renal Allograft Rejection Identified by DNA Microarray Profiling", The New England Journal of Medicine, Jul. 10, 2003, vol. 349, No. 2, pp. 125-138, Massachusetts Medical Society, Boston, MA, XP009045203, ISSN: 1533-4406.

Akalin, Enver; et al., "Gene Expression Analysis in Human Renal Allograft Biopsy Samples Using High-Density Oligoarray Technology", Transplantation, Sep. 15, 2001, vol. 72, No. 5, pp. 948-953, Williams and Wilkins, Baltimore, MD, XP002371138, ISSN: 0041-1337.

McMorrow, Isabel M.; et al., "New intra-renal graft genes associated with tolerance or rejection", Kidney International, vol. 61, symp. 1 (2002), pp. S85-S93, International Society of Nephrology, 2002, US, XP002434105, ISSN: 0085-2538.

Teramoto, Kenichi; et al., "DNA Synthesis in Hepatocytes During Liver Allograft Rejection in Rats", Transplantation, Aug. 1990, vol. 50, No. 2, pp. 199-201, Williams and Walkins, Baltimore, MD, XP009083910, ISSN: 0041-1337.

Gronowitz, J. S.; et al., "Serum Thymidine Kinase in Transplant Patients: Its Relation to Cytomegalovirus Activity, Renal Transplant Rejection and its Use for Monitoring of Antiviral Therapy", Annals of Clinical Research, 1986, vol. 18, No. 2, pp. 71-75, Helsinki, FI, XP009083909, ISSN: 0003-4762.

Fujiwaki, Ritsuto; et al., "Thymidine Kinase in Epithelial Ovarian Cancer: Relationship with the Other Pyrimidine Pathway Enzymes", Int. J. Cancer, May 20, 2002, vol. 99, No. 3, pp. 328-335, Publication of the International Union Against Cancer, XP002434106, ISSN: 0020-7136.

Database Embl [Online], "Thymidine Kinase, Cytosolic (human), mRNA Sequence", Feb. 5, 1998, 2pages, XP002434108, Database accession No. AA778098.

"Supplementary Partial European Search Report", European Patent Office, Jul. 3, 2007, PCT/US2005004799, 10 pages.

Chua M-S et al: "Applications of Microarrays to Renal Transplantation:Progress and Possibilities" Frontiers in Bioscience, Frontiers in Bioscience, Albertson, NY, US, vol. 8, Sep. 2003, pp. S913-S923.

Dugré F J et al: "Cytokine and cytotoxic molecule gene expression determined in peripheral blood mononuclear cells in the diagnosis of acute renal rejection." Transplantation Oct. 15, 2000, vol. 70, No. 7, Oct. 15, 2000, pp. 1074-1080.

Medbury H J et al: "The Cytokine and Histological Response in Islet Xenograft Rejection is Dependent Upon Species Combination" Transplantation, Williams and Wilkins, Baltimore, MD, US, vol. 64, No. 9, Nov. 15, 1997, pp. 1307-1314.

Simon T et al: "Serial peripheral blood perforin and granzyme B gene expression measurements for prediction of acute rejection in kidney graft recipients" American Journal of Transplantation, Blackwell Munksgaard,, DK, vol. 3, No. 9, Sep. 2003, pp. 1121-1127.

Wakui M et al: "Genes highly expressed in the early phase murine graft-versus-host rea" Biochemical and Biophysical Research Communications, Academic Press, San Diego, CA, US, vol. 282, No. 1, Mar. 23, 2001, pp. 200-206.

Hernandez-Fuentes; et al., "Immunologic monitoring", Immunological Reviews (2003), 196:247-264.

Thomson; et al., "Monitoring the Patient Off Immunosuppression" Transplantation (2001), 72(8):S13-S22.

Zhang; et al., "Microarray Analysis of Gene Expression in Peripheral Blood Mononuclear Cells Derived From Long-Surviving Renal Recipients", Transplantation Proceedings (2002), 34:1757-1759.

Butte; et al., "Protein microarrays discover angiotensinogen and PRKRIP1 as novel targets for autoantibodies in chronic renal disease", Mol Cell Proteomics (Mar. 2011), 10(3):M110.000497.

Cox; et al., "Altered modulation of WNT-beta-catenin and PI3K/Akt pathways in IgA nephropathy", Kidney Int (Aug. 2010), 78(4):396-407.

Dinarello; et al., "Anti-inflammatory Agents: Present and Future", Cell (Mar. 2010), 140(6):935-950.

Ismail; et al., "Important fluorinated drugs in experimental and clinical use", Journal of Fluorine Chemistry (Dec. 2002), 118(1):27-33.

Kalil; et al., "Meta-analysis: the efficacy of strategies to prevent organ disease by cytomegalovirus in solid organ transplant recipients", Ann Intern Med (Dec. 2005), 143(12):870-880.

Kaposztas; et al., "Impact of rituximab therapy for treatment of acute humoral rejection", Clin Transplant (Jan.-Feb. 2009), 23(1):63-73.

Metz; et al., "Application of proteomics in the discovery of candidate protein biomarkers in a diabetes autoantibody standardization program sample subset", J Proteome Res (Feb. 2008), 7(2):698-707.

Sato; et al., "Aberrant CD3- and CD3-mediated signaling events in cord blood T Cells are associated with dysfunctional regulation of Fas ligand-mediated cytotoxicity", The Journal of Immunology (Apr. 1999), 162 (8):4464-4471.

Sigdel; et al., "Profiling of autoantibodies in IgA nephropathy, an integrative antibiomics approach", Clin J Am Soc Nephrol (Dec. 2011), 6(12):2775-2784.

Alarcon; et al. "Time to renal disease and end-stage renal disease in PROFILE: a multiethnic lupus cohort", PLos Med (Oct. 2006), 3(10):e396.

Gwinner; et al. "Renal transplant rejection markers." World J Urol (Oct. 2007), 25(5):445-455.

Lang; et al. "DUSP meet immunology: dual specificity MAPK phosphatases in control of the inflammatory response", J Immunol (Dec. 2006), 177(11):7497-504.

Ling; et al. "Integrative urinary peptidomics in renal transplantation identifies biomarkers for acute rejection", J Am Soc Nephrol (Apr. 2010), 21(4):646-653.

Rotondi; et al. "High pretransplant serum levels of CXCL9 are associated with increased risk of acute rejection and graft failure in kidney graft recipients", Transpl Int (May 2010), 23(5):465-475.

Sigdel; et al. "Shotgun proteomics identifies proteins specific for acute renal transplant rejection", Proteomics Clin Appl (Jan. 2010), 4(1):32-47.

Voshol; et al. "Evaluation of biomarker discovery approaches to detect protein biomarkers of acute renal allograft rejection", J Proteome Res (Jul.-Aug. 2005), 4(4):1192-1199.

Communal; et al. "Reciprocal modulation of mitogen-activated protein kinases and mitogen-activated protein kinase phosphatase 1 and 2 in failing human myocardium", J Cardiac Failure (Apr. 2002), 8(2):86-92.

Lee et al., "Expression profiling of murine double-negative regularoty T cells suggest mechanisms for prolonged cardiac allograft survival", J. Immunol. (2005), 174(8):4535-4544.

Akalin; et al., "Bocking Cell Microtubule Assembly Inhibits the Alloimmune Response In Vitro and Prolongs Renal Allograft Survival by Inhibition of Th1 and Sparing of Th2 Cell Function In Vivo", Journal of the American Society of Nephrology (1995), 5(7):1418-1425.

(56) References Cited

OTHER PUBLICATIONS

Braud; et al., "Immunosuppresive Drug-Free Operational Immune Tolerance in Human Kidney Transplant Recipients: Part 1. Blood Gene Expression Statistical Analysis", Journal of Cellular Biochemistry (Apr. 2008),103(6):1681-1692.
Hauge; et al., "Characterization of the FAM110 gene family", Genomics (May 2007), 90:14-27.
Hillier; et al., "Generation and annotation of the DNA sequences of human chromosomes 2 and 4", Nature (2005), 434:724-731.
Matsuki; et al., "Novel regulation of MHC class II function in B cells", The EMBO Journal (Jan. 2007), 26:846-854.
Saint-Mezard; et al., "Analysis of independent microarray datasets of renal biopsies identifies a robust transcript signature of acute allograft rejection", Transplant International (Mar. 2009), 22(3):293-302.
Roedder; et al., "The pits and pearls in translating operational tolerance biomarkers into clinical practice", Current Opinion in Organ Transplantation (Dec. 2012), 17(6):655-662.
"Agilent-014850 whole human genome microarray 4x44K G4112F (Probe Name Version)", GEO (2008), XP002594592.
Brouard; et al., "Identification of a peripheral blood transcriptional biomarker panel associated with operational renal allograft tolerance", PNAS (2007), 104(39):15448-15453.
Carvalho-Gaspar; et al., "Chennokine gene expression during allograft rejection: Comparison of two quantitative PCR techniques", Journal of Immunological Methods (2005), 301(1-2):41-52.
Farivar; et al., "The role of CC and CXC chemokines in cardiac allograft rejection in rats", Experimental and Molecular Pathology (2005), 78(3):171-176.
Gimino; et al., Gene Expression Profiling of Broncholveolar Lavage Cells in Acute Lung Rejection, American Journal of Respiratory and Critical Care Medicine (2003), 168:1237-1242.
Horwitz; et al., "Detection of Cardiac Allograft Rejection and Response to Immunosuppressive Therapy with Peripheral Blood Gene Expression," Circulation (2004), 110:3815-3821.
Jevnikar; et al., "Late Kidney Allograft Loss: What We Know About It, and What We Can Do About It", Clin J Am Soc Nephrol (2008), 3(S56-S67).
Joosten; et al., "Chronic Renal Allograft Rejection: Pathophysiologic Considerations", Kidney International (2005), 68:1-13.
Li; et al. "Identifying compartment-specific non-HLA targets after renal transplantation by integrating transcriptome and "antibodyome" measures", PNAS (2009), 106(11):4148-4153.
Mansfield; et al., "Arraying the Orchestration of Allograft Pathology", American Journal of Transplantation (2004), 4(6):853-62.
Marsden, "Predicting Outcomes after Renal Transplantation—New Tools and Old Tools," The New England Journal of Medicine (2003), 349(2):182-184.
Midha; et al., "Chemokine Expression in Nerve Allografts," Neurosurgery (2004), 54(6):1472-149.
O'Riordan; et al., "Bioinformatic Analysis of the Urine Proteome of Acute Allograft Rejection," Journal of American Society of Nephrology (2004), 15:3240-3248.
Sarwal; et al., "Integrative Genomics to Identify Non-HLA Allogenic Kidney-Specific Targets after Kidney Transplantation", Transplantation (2008), 86(25):13, Oral Abstracts, downloaded Apr. 6, 2010.
Scherer; et al., "Early Prognosis of the Development of Renal Chronic Allograft Rejection by Gene Expression Profiling of Human Protocol Biopsies", Transplantation (2003), 75(8):1323-30.
Serody; et al., "T-lymphocyte production of macrophage inflammatory protein-lalpha is critical to the recruitment of CD8(+) T cells to the liver, lung, and spleen during graft-versus-host disease", Blood (2000), 96(9):2973-2980.
Shi; et al., "[Clinical significance of RANTES and MIP-1 alpha in acute rejection episode in kidney transplantation]", Zhongguo Yi Xue Ke Xue Yuan Xue Bao (2004), 26(1):70-72.
Whitfield; et al., "Systemic and Cell Type-Specific Gene Expression Patterns in Scleroderma Skin," Proc. Natl. Acad Sci. (2003), 100(21):12319-12324.
Li; et al., "A Peripheral Blood Diagnostic Test for Acute Rejection in Renal Transplantation", American Journal of Transplantation (Oct. 2012), 12(10):2710-2718.
Nesslinger; et al., "A viral vaccine encoding prostate-specific antigen induces antigen spreading to a common set of self-proteins in prostate cancer patients", Clinical Cancer Research (Aug. 2010), 16(15):4046-4056.
"Affymetrix Human genome U133 Plus 2.0 Array", Gene Expression Omnibus (Nov. 2003), XP002627319, 3pgs.
Al-Lamki; et al., "Expression of Tumor Necrosis Factor Receptors in Normal Kidney and Rejecting Renal Transplants", Laboratory Investigation (Nov. 2001), 81(11): 1503-1515.
Chen; et al., "Differentially Expressed RNA from Public Microarray Data Identifies Serum Protein Biomarkers for Cross-Organ Transplant Rejection and Other Conditions", PLOS Computational Biology (Sep. 2010), 6(9):e1000940.
Hardiman, "Microarray platforms—comparisons and contrasts", Pharmacogenomics (Jan. 2004), 5(5): 487-502.
Hauser; et al., "Prediction of Acute Renal Allograft Rejection by Urinary Monokine Induced by IFN-gamma (MIG)", The American Society of Nephrology (Jan. 2005), 16(6):1849-1858.
Hidalgo; et al., "The Transcriptome of Human Cytotoxic T Cells: Measuring the Burden of CTL-Associated Transcripts in Human Kidney Transplants", American Journal of Transplantation (Mar. 2008), 8(3):637-646.
Mengel; et al., "Scoring Total Inflammation Is Superior to the Current Banff Inflammation Score in Predicting Outcome and the Degree of Molecular Disturbance in Renal Allografts", American Journal of Transplantation (Aug. 2009), 9(8):1859-1867.
Morgun; et al., "Molecular Profiling Improves Diagnoses of Rejected and Infection in Transplanted Organs", Circulation Research (Jun. 2006), 98(12):e74-83.
"GeneChip 3' IVT PLUS Reagent Kit", Affymetrix (2013), User Manual, 45 pgs.
Famulski; et al., "Changes in the Transcriptome in Allograft Rejection: IFN-.gamma.-Induced Transcripts in Mouse Kidney Allografts", American Journal of Transplantation (Jun. 2006), 6(6):1342-1354.

* cited by examiner

FIG. 1
Table 1.

| Clone | Accession | Gene | Description | Fold-Diff |
|---|---|---|---|---|
| IMAGE:379920 | AA778098 | TK1 | thymidine kinase 1, soluble | 4.60 |
| IMAGE:436094 | AA700832 | RBP1 | retinol binding protein 1, cellular | 3.47 |
| IMAGE:2108366 | AI392840 | EPHA2 | EphA2 | 3.75 |
| IMAGE:210717 | H64346 | SDC2 | syndecan 2 (heparan sulfate proteoglycan 1, fibroglycan) | 4.45 |
| IMAGE:2557762 | AW050510 | PYCR1 | pyrroline-5-carboxylate reductase 1 | 3.17 |
| IMAGE:196992 | R93124 | AKR1C1 | aldo-keto reductase family 1, member C1 | 3.97 |
| IMAGE:783936 | AA443405 | SLC7A7 | solute carrier family 7 (cationic amino acid transporter) | 4.07 |
| IMAGE:1577805 | AA954999 | CDH2 | cadherin 2, type 1, N-cadherin (neuronal) | 4.26 |
| IMAGE:753038 | AA436460 | KIFC3 | kinesin family member C3 | 2.83 |
| IMAGE:436121 | AA701996 | SLC7A7 | solute carrier family 7 (cationic amino acid transporter) | 4.33 |
| IMAGE:122159 | T98611 | COL3A1 | collagen, type III, alpha 1 | 4.83 |
| IMAGE:2108490 | AI394016 | C20orf42 | chromosome 20 open reading frame 42 | 2.94 |
| IMAGE:526657 | AA128607 | TCEB3 | transcription elongation factor B (SIII) | 6.45 |
| IMAGE:486110 | AA040703 | PFN2 | profilin 2 | 4.47 |
| IMAGE:1283012 | AA745260 | CCNB2 | cyclin B2 | 5.98 |
| IMAGE:1474174 | AA936799 | MMP2 | matrix metalloproteinase 2 (gelatinase A, 72kDa gelatinase) | 3.39 |
| IMAGE:2545705 | AI969128 | CNN3 | calponin 3, acidic | 4.41 |
| IMAGE:2457449 | AI932735 | CCNB2 | cyclin B2 | 4.26 |
| IMAGE:897956 | AA598817 | PRAME | preferentially expressed antigen in melanoma | 2.80 |
| IMAGE:451907 | AA706968 | ZWINT | ZW10 interactor | 3.47 |
| IMAGE:307471 | N93505 | TM4SF2 | transmembrane 4 superfamily member 2 | 3.04 |
| IMAGE:139009 | R62612 | FN1 | fibronectin 1 | 7.65 |
| IMAGE:2109103 | AI380951 | COL6A3 | collagen, type VI, alpha 3 | 3.73 |
| IMAGE:897910 | AA598653 | OSF-2 | osteoblast specific factor 2 (fasciclin I-like) | 7.88 |
| IMAGE:377384 | AA055076 | NR2F2 | nuclear receptor subfamily 2, group F, member 2 | 4.32 |
| IMAGE:785933 | AA448569 | SRPX | sushi-repeat-containing protein, X chromosome | 4.15 |
| IMAGE:241029 | H81023 | STK12 | serine/threonine kinase 12 | 2.99 |
| IMAGE:199367 | R95691 | SERPINE2 | serine (or cysteine) proteinase inhibitor, clade E | 6.36 |
| IMAGE:74537 | T59043 | AFP | alpha-fetoprotein | 4.77 |
| IMAGE:2449395 | AI924357 | AKR1C1 | aldo-keto reductase family 1, member C1 | 3.46 |
| IMAGE:815526 | AA456878 | MYBL2 | v-myb myeloblastosis viral oncogene homolog (avian)-like 2 | 3.18 |
| IMAGE:784593 | AA443302 | PDE1A | phosphodiesterase 1A, calmodulin-dependent | 2.84 |
| IMAGE:360254 | AA012892 | CYR61 | cysteine-rich, angiogenic inducer, 61 | 9.01 |
| IMAGE:1517595 | AA903137 | MELK | maternal embryonic leucine zipper kinase | 3.59 |
| IMAGE:2577230 | AW075585 | TNC | tenascin C (hexabrachion) | 3.29 |
| IMAGE:758088 | AA426421 | CALD1 | caldesmon 1 | 2.98 |
| IMAGE:490995 | AA136707 | PLOD2 | procollagen-lysine, 2-oxoglutarate 5-dioxygenase | 3.09 |
| IMAGE:250654 | H95959 | SPARC | secreted protein, acidic, cysteine-rich (osteonectin) | 2.89 |
| IMAGE:344430 | W73473 | BMP7 | bone morphogenetic protein 7 (osteogenic protein 1) | 2.95 |
| IMAGE:1316861 | AA768291 | MELK | maternal embryonic leucine zipper kinase | 3.54 |
| IMAGE:898092 | AA598794 | CTGF | connective tissue growth factor | 6.49 |
| IMAGE:1307938 | AA767775 | TAL2 | T-cell acute lymphocytic leukemia 2 | 2.17 |
| IMAGE:133273 | R26732 | PMP22 | peripheral myelin protein 22 | 3.58 |
| IMAGE:1845885 | AI218117 | TYR | tyrosinase (oculocutaneous albinism IA) | 2.22 |

FIG. 1 (Continued)

Table 1

| Clone | Accession | Gene | Description | Fold-Diff |
|---|---|---|---|---|
| IMAGE:1250917 | AA731503 | FLJ20311 | hypothetical protein FLJ20311 | 2.81 |
| IMAGE:346696 | W72159 | TEAD4 | TEA domain family member 4 | 3.31 |
| IMAGE:878564 | AA775872 | GPC3 | glypican 3 | 3.56 |
| IMAGE:744647 | AA621315 | CTNNAL1 | catenin (cadherin-associated protein), alpha-like 1 | 2.63 |
| IMAGE:359412 | AA010487 | CCND2 | cyclin D2 | 6.77 |
| IMAGE:2569190 | AW073393 | FSTL1 | follistatin-like 1 | 4.03 |
| IMAGE:124345 | R02117 | CENPF | centromere protein F, 350/400ka (mitosin) | 3.02 |
| IMAGE:378461 | AA775616 | SPP1 | secreted phosphoprotein 1 (osteopontin, T-cell activation 1) | 4.90 |
| IMAGE:460470 | AA677687 | C4BPB | complement component 4 binding protein, beta | 2.25 |
| IMAGE:116743 | T89453 | FADS1 | fatty acid desaturase 1 | 7.70 |
| IMAGE:358168 | W95586 | MGC9850 | hypothetical protein MGC9850 | 4.46 |
| IMAGE:809473 | AA443119 | PTRF | polymerase I and transcript release factor | 2.75 |
| IMAGE:786673 | AA451903 | RBM9 | RNA binding motif protein 9 | 2.60 |
| IMAGE:68950 | T54121 | CCNE1 | cyclin E1 | 2.61 |
| IMAGE:2057931 | AI340883 | TACSTD1 | tumor-associated calcium signal transducer 1 | 3.68 |
| IMAGE:526184 | AA076645 | RAB21 | RAB21, member RAS oncogene family | 5.23 |
| IMAGE:781047 | AA430092 | BUB1 | BUB1 budding uninhibited by benzimidazoles 1 | 3.61 |
| IMAGE:788566 | AA452826 | PCP4 | Purkinje cell protein 4 | 3.75 |
| IMAGE:2391979 | AI738499 | DHRS2 | dehydrogenase/reductase (SDR family) member 2 | 10.27 |
| IMAGE:2019101 | AI359985 | AGT | angiotensinogen (serine (or cysteine) proteinase inhibitor | 3.85 |
| IMAGE:753184 | AA400464 | SOX9 | SRY (sex determining region Y) | 2.64 |
| IMAGE:450533 | AA704242 | SERPINA3 | serine proteinase inhibitor(antitrypsin) | 3.87 |
| IMAGE:142788 | R71093 | SERPINH2 | serine proteinase inhibitor (heat shock protein 47) | 3.64 |
| IMAGE:1269639 | AA714672 | M96 | metal response element binding transcription factor 2 | 3.58 |
| IMAGE:1871508 | AI262459 | TM4SF5 | transmembrane 4 superfamily member 5 | 2.45 |
| IMAGE:378488 | AA777187 | CYR61 | cysteine-rich, angiogenic inducer, 61 | 4.13 |
| IMAGE:625016 | AA181040 | SPARC | secreted protein, acidic, cysteine-rich (osteonectin) | 2.72 |
| IMAGE:2019116 | AI359981 | SOX3 | SRY (sex determining region Y)-box 3 | 2.97 |
| IMAGE:487878 | AA045463 | SPARC | secreted protein, acidic, cysteine-rich (osteonectin) | 2.92 |
| IMAGE:772437 | AA405486 | KIAA0638 | KIAA0638 protein | 2.43 |
| IMAGE:212188 | H68848 | APOH | apolipoprotein H (beta-2-glycoprotein I) | 4.84 |
| IMAGE:665356 | AA194983 | TNFRSF11B | tumor necrosis factor receptor 11b (osteoprotegerin) | 2.26 |
| IMAGE:774471 | AA429989 | LAMB1 | laminin, beta 1 | 3.04 |
| IMAGE:2108629 | AI492226 | C20orf42 | chromosome 20 open reading frame 42 | 2.12 |
| IMAGE:725680 | AA394236 | TFAP2C | transcription factor AP-2 gamma (activating enhancer) | 5.04 |
| IMAGE:624627 | AA187351 | RRM2 | ribonucleotide reductase M2 polypeptide | 2.88 |
| IMAGE:2569884 | AW084720 | C1S | complement component 1, s subcomponent | 2.38 |
| IMAGE:855563 | AA664212 | ERBB3 | v-erb-b2 erythroblastic leukemia viral oncogene homolog 3 | 2.31 |
| IMAGE:1584142 | AA972716 | GAGEB1 | G antigen, family B, 1 (prostate associated) | 2.59 |
| IMAGE:209066 | H63492 | STK6 | serine/threonine kinase 6 | 3.62 |
| IMAGE:342640 | W68219 | KIAA0101 | KIAA0101 gene product | 3.37 |
| IMAGE:897788 | AA598513 | PTPRF | protein tyrosine phosphatase, receptor type, F | 3.39 |
| IMAGE:796694 | AA460685 | BIRC5 | baculoviral IAP repeat-containing 5 (survivin) | 2.33 |
| IMAGE:796606 | AA460520 | CDV-1 | carnitine deficiency-associated gene | 2.10 |
| IMAGE:1323591 | AA858026 | SERPINA5 | serine (or cysteine) proteinase inhibitor | 4.79 |
| IMAGE:50562 | H16793 | C8orf4 | chromosome 8 open reading frame 4 | 2.80 |
| IMAGE:1475476 | AA857809 | MAGEA4 | melanoma antigen, family A, 4 | 2.72 |
| IMAGE:121551 | T97710 | LAD1 | ladinin 1 | 2.39 |
| IMAGE:683100 | AA213393 | CCNA2 | cyclin A2 | 2.61 |

FIG. 1 (Continued)

Table 1

| Clone | Accession | Gene | Description | Fold-Diff |
|---|---|---|---|---|
| IMAGE:2063390 | AI375135 | AMBP | alpha-1-microglobulin/bikunin precursor | 5.72 |
| IMAGE:839991 | AA490172 | COL1A2 | collagen, type I, alpha 2 | 2.49 |
| IMAGE:1948085 | AI352345 | CBR3 | carbonyl reductase 3 | 2.28 |
| IMAGE:377461 | AA055368 | CAV1 | caveolin 1, caveolae protein, 22kDa | 4.94 |
| IMAGE:1302907 | AA732416 | PARVG | parvin, gamma | 3.64 |
| IMAGE:626001 | AA187933 | TAZ | transcriptional co-activator with PDZ-binding motif (TAZ) | 2.26 |
| IMAGE:263716 | H99676 | COL6A1 | collagen, type VI, alpha 1 | 3.19 |
| IMAGE:884418 | AA773070 | MYO5B | myosin VB | 2.04 |
| IMAGE:1472743 | AA872397 | LGALS2 | lectin, galactoside-binding, soluble, 2 (galectin 2) | 2.86 |
| IMAGE:344139 | W69790 | DOC1 | downregulated in ovarian cancer 1 | 2.34 |
| IMAGE:686172 | AA262211 | KIAA0008 | Drosophila discs large-1 tumor supressor-like | 2.09 |
| IMAGE:290378 | N64508 | PODXL | podocalyxin-like | 2.59 |
| IMAGE:2092597 | AI381509 | GAGE8 | G antigen 8 | 3.81 |
| IMAGE:898286 | AA598974 | CDC2 | cell division cycle 2, G1 to S and G2 to M | 2.33 |
| IMAGE:773495 | AA427924 | MGC10724 | hypothetical protein MGC10724 | 3.64 |
| IMAGE:212429 | H69531 | TF | transferrin | 2.99 |
| IMAGE:2543464 | AW029498 | SERPINA3 | serine (or cysteine) proteinase inhibitor, clade A | 5.04 |
| IMAGE:825470 | AA504348 | TOP2A | topoisomerase (DNA) II alpha 170kDa | 2.45 |
| IMAGE:300411 | N80273 | CCL19 | chemokine (C-C motif) ligand 19 | 2.04 |
| IMAGE:2489436 | AI972269 | MYLK | myosin, light polypeptide kinase | 1.91 |
| IMAGE:489519 | AA099153 | TIMP3 | tissue inhibitor of metalloproteinase 3 | 2.41 |
| IMAGE:2568350 | AW070825 | KRT19 | keratin 19 | 5.68 |
| IMAGE:234237 | H69334 | PIR | Pirin | 2.72 |
| IMAGE:810131 | AA464250 | KRT19 | keratin 19 | 2.83 |
| IMAGE:2139448 | AI470584 | TNRC9 | trinucleotide repeat containing 9 | 1.98 |
| IMAGE:2223790 | AI571948 | TFF1 | trefoil factor 1 (breast cancer, estrogen-inducible) | 2.41 |
| IMAGE:33603 | R19521 | GPRC5B | G protein-coupled receptor, family C5B | 2.40 |
| IMAGE:782575 | AA447522 | HSJ001348 | cDNA for differentially expressed CO16 gene | 2.03 |
| IMAGE:49569 | H15115 | KIAA1026 | KIAA1026 protein | 1.96 |
| IMAGE:1335954 | AA810530 | POLQ | polymerase (DNA directed), theta | 2.41 |
| IMAGE:148800 | H13424 | N33 | Putative prostate cancer tumor suppressor | 3.08 |
| IMAGE:343821 | W69496 | TYRO3 | TYRO3 protein tyrosine kinase | 2.32 |
| IMAGE:2021931 | AI361763 | B4GALT2 | UDP-Gal:betaGlcNAc beta 1,4- galactosyltransferase | 2.88 |
| IMAGE:1493107 | AA876375 | LTB4DH | leukotriene B4 12-hydroxydehydrogenase | 2.61 |
| IMAGE:45099 | H05140 | RGN | regucalcin (senescence marker protein-30) | 1.92 |
| IMAGE:29205 | R14517 | MIG2 | mitogen inducible 2 | 2.68 |
| IMAGE:487297 | AA040613 | CAP2 | adenylyl cyclase-associated protein 2 | 2.73 |
| IMAGE:141815 | R70684 | JAG1 | jagged 1 (Alagille syndrome) | 2.29 |
| IMAGE:1272470 | AA743293 | FOXM1 | forkhead box M1 | 2.52 |
| IMAGE:782730 | AA447978 | ALDH1A2 | aldehyde dehydrogenase 1 family, member A2 | 2.59 |
| IMAGE:1241341 | AA714513 | HLA-DRB3 | major histocompatibility complex, class II, DR beta 3 | 2.26 |
| IMAGE:898062 | AA598776 | CDC20 | CDC20 cell division cycle 20 homolog (S. cerevisiae) | 2.06 |
| IMAGE:66406 | T66935 | DKFZp762E1312 | hypothetical protein DKFZp762E1312 | 2.48 |
| IMAGE:41648 | R52795 | IL13RA2 | interleukin 13 receptor, alpha 2 | 3.28 |
| IMAGE:2308409 | AI653116 | KIAA1077 | sulfatase FP | 3.22 |
| IMAGE:1235082 | AA713690 | BRRN1 | barren homolog (Drosophila) | 2.32 |
| IMAGE:827384 | AA669106 | UHRF1 | ubiquitin-like, containing PHD/RING finger domains, 1 | 2.33 |
| IMAGE:1913366 | AI308916 | PRSS3 | protease, serine, 3 (mesotrypsin) | 2.81 |
| IMAGE:714106 | AA284668 | PLAU | plasminogen activator, urokinase | 2.08 |

FIG. 1 (Continued)

Table 1

| Clone | Accession | Gene | Description | Fold Diff |
|---|---|---|---|---|
| IMAGE:32983 | R18944 | SIN3A | SIN3 homolog A, transcriptional regulator (yeast) | 4.99 |
| IMAGE:1284490 | AA744546 | TTK | TTK protein kinase | 2.40 |
| IMAGE:344854 | W72972 | ANKRD3 | ankyrin repeat domain 3 | 2.22 |
| IMAGE:1056107 | AA628360 | C20orf16 | chromosome 20 open reading frame 16 | 2.18 |
| IMAGE:760299 | AA425947 | DKK3 | dickkopf homolog 3 (Xenopus laevis) | 3.01 |
| IMAGE:809910 | AA464416 | IFITM3 | interferon induced transmembrane protein 3 (1-8U) | 3.06 |
| IMAGE:2488862 | AI971229 | FKBP9 | FK506 binding protein 9, 63 kDa | 2.65 |
| IMAGE:141314 | R63811 | LMCD1 | LIM and cysteine-rich domains 1 | 2.32 |
| IMAGE:1597856 | AA961402 | APOA2 | apolipoprotein A-II | 2.67 |
| IMAGE:2488265 | AI970855 | SEMA3F | sema domain, immunoglobulin domain (Ig) | 2.45 |
| IMAGE:2012757 | AI356709 | D2S448 | Melanoma associated gene | 2.25 |
| IMAGE:684238 | AA251325 | MCM2 | MCM2 minichromosome maintenance deficient 2, mitotin | 2.50 |
| IMAGE:259291 | N29501 | ITGB5 | integrin, beta 5 | 2.26 |
| IMAGE:1550909 | AA913206 | GAGE8 | G antigen 8 | 2.26 |
| IMAGE:135221 | R32848 | S100P | S100 calcium binding protein P | 2.23 |
| IMAGE:1241524 | AA729003 | TCL1A | T-cell leukemia/lymphoma 1A | 2.33 |
| IMAGE:795730 | AA460282 | EFS2 | signal transduction protein (SH3 containing) | 1.87 |
| IMAGE:40580 | R55130 | HTR2A | 5-hydroxytryptamine (serotonin) receptor 2A | 1.79 |
| IMAGE:897865 | AA598640 | MID1 | midline 1 (Opitz/BBB syndrome) | 1.89 |
| IMAGE:2018976 | AI362866 | PTTG1 | pituitary tumor-transforming 1 | 2.22 |
| IMAGE:50182 | H17882 | KAL1 | Kallmann syndrome 1 sequence | 1.84 |
| IMAGE:47142 | H10964 | PEX12 | peroxisomal biogenesis factor 12 | 2.20 |
| IMAGE:549383 | AA081414 | PLAB | prostate differentiation factor | 2.37 |
| IMAGE:815709 | AA485172 | HLA-DOA | major histocompatibility complex, class II, DO alpha | 1.92 |
| IMAGE:682989 | AA210804 | PAICS | phosphoribosylaminoimidazole carboxylase | 2.29 |
| IMAGE:773322 | AA425419 | SHOX2 | short stature homeobox 2 | 1.96 |
| IMAGE:293339 | N64741 | SNAI2 | snail 2 | 2.94 |
| IMAGE:512337 | AA057826 | RPS5 | ribosomal protein S5 | 2.44 |
| IMAGE:927027 | AA535146 | CCL20 | chemokine (C-C motif) ligand 20 | 2.22 |
| IMAGE:375682 | AA032221 | STEAP | six transmembrane epithelial antigen of the prostate | 3.12 |
| IMAGE:753248 | AA406231 | DAAM2 | dishevelled associated activator of morphogenesis 2 | 1.96 |
| IMAGE:739155 | AA421819 | CDH6 | cadherin 6, type 2, K-cadherin (fetal kidney) | 2.92 |
| IMAGE:2017415 | AI369629 | CENPA | centromere protein A, 17kDa | 4.10 |
| IMAGE:1558642 | AA976544 | MLPH | melanophilin | 2.91 |
| IMAGE:1357100 | AA832260 | SLC2A5 | solute carrier f(facilitated glucose/fructose transporter) | 1.86 |
| IMAGE:1407750 | AA861203 | IGFBP3 | insulin-like growth factor binding protein 3 | 3.40 |
| IMAGE:813387 | AA455538 | NQO1 | NAD(P)H dehydrogenase, quinone 1 | 2.44 |
| IMAGE:2428020 | AI870548 | HP | haptoglobin | 2.51 |
| IMAGE:1356393 | AA831559 | DDR1 | discoidin domain receptor family, member 1 | 2.49 |
| IMAGE:2018154 | AI364521 | ETFB | electron-transfer-flavoprotein, beta polypeptide | 1.87 |
| IMAGE:1234404 | AA687354 | CD22 | CD22 antigen | 2.24 |
| IMAGE:796398 | AA459941 | ZIM2 | zinc finger, imprinted 2 | 2.82 |
| IMAGE:1928791 | AI313387 | F3 | coagulation factor III (thromboplastin, tissue factor) | 2.24 |
| IMAGE:246524 | N53057 | CHEK1 | CHK1 checkpoint homolog (S. pombe) | 1.91 |
| IMAGE:2494168 | AI986336 | FLJ20151 | hypothetical protein FLJ20151 | 2.23 |
| IMAGE:434768 | AA701860 | FST | follistatin | 2.38 |
| IMAGE:2016775 | AI356028 | GPRC5B | G protein-coupled receptor, family C, group 5, member B | 2.14 |
| IMAGE:811740 | AA463257 | ITGA2 | integrin, alpha 2 (CD49B, subunit of VLA-2 receptor) | 1.94 |
| IMAGE:2569769 | AW084638 | CA2 | carbonic anhydrase II | 1.97 |

FIG. 1 (Continued)

Table 1

| Clone | Accession | Gene | Description | Fold-Diff |
|---|---|---|---|---|
| IMAGE:878438 | AA670362 | TEAD2 | TEA domain family member 2 | 2.23 |
| IMAGE:773330 | AA425450 | GPNMB | glycoprotein (transmembrane) nmb | 2.25 |
| IMAGE:347560 | W81317 | H1FX | H1 histone family, member X | 1.79 |
| IMAGE:1470446 | AA864299 | FLJ32987 | proapoptotic caspase adaptor protein | 2.10 |
| IMAGE:753969 | AA478949 | DLG5 | discs, large (Drosophila) homolog 5 | 1.87 |
| IMAGE:2014382 | AI362029 | NR2F1 | nuclear receptor subfamily 2, group F, member 1 | 2.02 |
| IMAGE:770859 | AA434397 | ITGB5 | integrin, beta 5 | 2.27 |
| IMAGE:2409751 | AI816969 | ESPL1 | extra spindle poles like 1 (S. cerevisiae) | 1.83 |
| IMAGE:840493 | AA485893 | RNASE1 | ribonuclease, RNase A family, 1 (pancreatic) | 3.00 |

Figure 2
Table 2.

| Gene category/class | # cDNA | Most highly-differentially expressed gene in the category | | | Fold* |
|---|---|---|---|---|---|
| | | Accession. | Clone.ID | Gene | |
| Apoptosis | 5 | AA864299 | IMAGE:1470446 | PACAP proapoptotic caspase adaptor protein | 2.22 |
| B-Cell related | 27 | AI186799 | IMAGE:1745349 | MYOM2 myomesin (M-protein) 2, 165kDa | 3.6 |
| Cell adhesion/calcium channel | 8 | AA954999 | IMAGE:1577805 | CDH2 cadherin 2, type 1, N-cadherin (neuronal) | 3.61 |
| Cell cycle genes | 33 | AA010487 | IMAGE:359412 | CCND2 cyclin D2 | 8.19 |
| Cell matrix | 67 | AA598653 | IMAGE:897910 | OSF-2 osteoblast specific factor 2 | 9.71 |
| Cell signaling | 41 | AI394733 | IMAGE:2109760 | SLC38A6 solute carrier family 38, member 6 | 6.37 |
| Chemokines | 17 | AI950929 | IMAGE:2548121 | C1S complement component 1s | 4.55 |
| Detoxification | 28 | R93124 | IMAGE:196992 | AKR1C-pseudo-chlordecone reductase | 4.63 |
| DNA replication | 32 | AI369629 | IMAGE:2017415 | CENPA centromere protein A, Core histone | 4.94 |
| ESTs or unknown cDNAs | 181 | AI738499 | IMAGE:2391979 | cDNA FLJ20338 fis, clone HEP12179 | 12.60 |
| Growth factors | 8 | AA012892 | IMAGE:360254 | CYR61 cysteine-rich, angiogenic inducer 61 | 10.83 |
| Lipid/cholesterol | 8 | T89453 | IMAGE:116743 | FADS1 fatty acid desaturase 1 | 8.44 |
| Oncogenes | 17 | AA076645 | IMAGE:526184 | RAB21, member RAS oncogene family | 6.35 |
| Other genes of known function | 22 | AA452826 | IMAGE:788566 | PCP4 Purkinje cell protein 4 | 4.41 |
| Protease inhibitors | 18 | R95691 | IMAGE:199367 | SERPINE2 Serine/cysteine proteinase inhibitor, E2 | 6.12 |
| Protein kinases | 25 | AA832386 | IMAGE:1357548 | STK6 serine/threonine kinase 6 IPL1-related kinase | 4.54 |
| Ribosomal genes | 3 | AA057826 | IMAGE:512337 | RPS5 ribosomal protein S5 | 2.71 |
| T-Cell related | 17 | AA775616 | IMAGE:378461 | SPP1 secreted T-lymphocyte activation 1 | 5.79 |
| Transcription factors | 26 | AA128607 | IMAGE:526657 | TCEB3 transcription elongation factor B (SIII) | 7.37 |

*1. Fold reported is the average expression level in PBL from OT patient group relative to CR.

FIG. 3
Table 3.

| Accession | Clone ID | Gene | Fold-change | Cellular role |
|---|---|---|---|---|
| Apoptosis | | | | |
| AA460685 | IMAGE:796694 | BIRC5 | 2.65 | Inhibitor of Apoptosis domain |
| AA864299 | IMAGE:1470446 | PACAP | 2.22 | Proapoptotic caspase adaptor |
| T50675 | IMAGE:72778 | CASP7 | 2.06 | Apoptosis-related cysteine protease |
| AA125792 | IMAGE:502664 | RIS1 | 2.28 | Ras-induced senescence 1 |
| H05140 | IMAGE:45099 | RGN | 2.36 | Senescence marker protein-30 |
| AI886854 | IMAGE:2413733 | FAIM2 | 1.56 | Fas apoptotic inhibitory molecule |
| AA291229 | IMAGE:700619 | BNIP3 | 1.88 | Pro-apoptotic 19K/Bcl-2-interacting protein |
| Complement | | | | |
| AI950929 | IMAGE:2548121 | C1S | 4.55 | Complement component 1s |
| T69603 | IMAGE:83549 | C1R | 1.91 | Complement component 1r |
| T68274 | IMAGE:83210 | C8B | 1.5 | Complement component 8 |
| AA746481 | IMAGE:1251210 | CD59 | 2.61 | Complement membrane attack regulator |
| Serine/cysteine protease inhibitors | | | | |
| R95691 | IMAGE:199367 | SERPINE2 | 6.11 | Plasminogen activator inhibitor |
| AA858026 | IMAGE:1323591 | SERPINA5 | 5.77 | a-1 antiproteinase, antitrypsin |
| AA704242 | IMAGE:450533 | SERPINA3 | 4.52 | a-1 antiproteinase, antitrypsin |
| R71093 | IMAGE:142788 | SERPINH2 | 4.36 | Heat shock protein 47 |
| AI084671 | IMAGE:1681489 | SERPINE1 | 1.82 | Plasminogen activator inhibitor |
| T62086 | IMAGE:85690 | SERPIND1 | 1.45 | Heparin cofactor/ proteinase inhibitor |
| Growth factors/receptors | | | | |
| AA012892 | IMAGE:360254 | CYR61 | 10.83 | Angiogenic inducer |
| AA463257 | IMAGE:811740 | ITGA2 | 1.93 | Integrin, alpha 2/VLA-2 receptor |
| W73473 | IMAGE:344430 | BMP7 | 3.19 | TGF-beta family osteogenic protein |
| AA598794 | IMAGE:898092 | CTGF | 7.86 | Connective tissue growth factor |
| Cyclins | | | | |
| AA010487 | IMAGE:359412 | CCND2 | 8.19 | Cyclin D2 |
| AA745260 | IMAGE:1283012 | CCNB2 | 7.27 | Cyclin B2 |
| AA213393 | IMAGE:683100 | CCNA2 | 3.04 | Cyclin A2 |
| T54121 | IMAGE:68950 | CCNE1 | 2.68 | Cyclin E1 |
| Lipid metabolism/cholesterol transport | | | | |
| T89453 | IMAGE:116743 | FADS1 | 8.44 | Fatty acid desaturase 1 |
| H68848 | IMAGE:212188 | APOH | 5.83 | Apolipoprotein H |
| AA961402 | IMAGE:1597856 | APOA2 | 3.06 | Apolipoprotein A-II |
| R00706 | IMAGE:123474 | SCD | 1.6 | Stearoyl-CoA desaturase |
| T53121 | IMAGE:68504 | APOB | 2.14 | Apolipoprotein B |
| NM_000237 | LCP:7381 | LPL | 1.96 | Lipoprotein lipase |
| Calcium dependenT-cell-cell adhesion | | | | |
| AA954999 | IMAGE:1577805 | CDH2 | 3.61 | Cadherin 2, type 1, N-cadherin |
| AA421819 | IMAGE:739155 | CDH6 | 3.58 | Cadherin 6, type 2, K-cadherin |
| AW007700 | IMAGE:2506265 | CACNA2D2 | 3.2 | Calcium channel, voltage-dependent |
| R32848 | IMAGE:135221 | S100P | 2.64 | S100 calcium binding protein |
| Cell surface stimulation | | | | |
| H64346 | IMAGE:210717 | SDC2 | 5.25 | Syndecan 2 (fibroglycan) |
| AI969128 | IMAGE:2545705 | CNN3 | 5.21 | Calponin 3, acidic |
| AA936799 | IMAGE:1474174 | MMP2 | 4.45 | Matrix metalloproteinase 2 |
| AA775447 | IMAGE:878182 | A2M | 4.08 | Alpha-2-macroglobulin |
| AA478662 | IMAGE:754106 | TIMP3 | 3.33 | Tissue inhibitor of metalloproteinase 3 |
| R14517 | IMAGE:29205 | MIG2 | 3.21 | Mitogen inducible chemokine |

FIG. 3 (Continued)

Table 3

| Accession | Clone ID | Gene | Fold-change | Cellular role |
|---|---|---|---|---|
| Cell matrix/ structural proteins | | | | |
| AA598653 | IMAGE:897910 | OSF-2 | 9.71 | Osteoblast-specific factor/adhesion |
| R62612 | IMAGE:139009 | FN1 | 9.27 | Fibronectin 1 |
| AW070825 | IMAGE:2568350 | KRT19 | 6.88 | Keratin 19 |
| AA055368 | IMAGE:377461 | CAV1 | 5.92 | Caveolin 1, caveolae protein |
| T59043 | IMAGE:74537 | AFP | 5.49 | Alpha-fetoprotein |
| T98611 | IMAGE:122159 | COL3A1 | 5.45 | Collagen, type III, alpha 1 |
| AA040703 | IMAGE:486110 | PFN2 | 5.23 | Profilin 2 |
| AA701996 | IMAGE:436121 | DLK1 | 5.01 | Delta-like 1 homolog (Drosophila) |
| AI380951 | IMAGE:2109103 | COL6A3 | 4.47 | Collagen, type VI, alpha 3 |
| AA427924 | IMAGE:773495 | SPON1 | 4.42 | Spondin 1, extracellular matrix |
| R26732 | IMAGE:133273 | PMP22 | 3.97 | Peripheral myelin protein 22 |
| AW075585 | IMAGE:2577230 | TNC | 3.83 | Tenascin C (hexabrachion) |
| H99676 | IMAGE:263716 | COL6A1 | 3.54 | Collagen, type VI, alpha 1 |
| AA436460 | IMAGE:753038 | KIFC3 | 3.38 | Kinesin family member C3 |
| H69531 | IMAGE:212429 | TF | 3.23 | Transferrin |
| W73473 | IMAGE:344430 | BMP7 | 3.19 | Osteogenic protein - TGF-beta family |
| AA464250 | IMAGE:810131 | KRT19 | 2.91 | Keratin 19 |

METHODS AND COMPOSITIONS FOR DETERMINING A GRAFT TOLERANT PHENOTYPE IN A SUBJECT

CROSS-REFERENCE TO RELATED APPLICATIONS

Pursuant to 35 U.S.C. §119 (e), this application claims priority to the filing date of the U.S. Provisional Patent Application Ser. No. 60/571,471 filed May 14, 2004 and to the filing date of U.S. Provisional Patent Application Ser. No. 60/538,439 filed on Jan. 21, 2004; the disclosures of which are herein incorporated by reference.

FEDERALLY-SPONSORED RESEARCH OR DEVELOPMENT

This invention was made with Government support under contract HD033698 awarded by the National Institutes of Health. The Government has certain rights in this invention.

INTRODUCTION

Background of the Invention

Transplantation of a graft organ or tissue from a donor to a host patient is a feature of certain medical procedures and treatment protocols. Despite efforts to avoid graft rejection through host-donor tissue type matching, in transplantation procedures where a donor organ is introduced into a host, immunosuppressive therapy is generally required to the maintain viability of the donor organ in the host.

A variety of immunosuppressive agents have been employed in transplantation procedures, including azathioprine, methotrexate, cyclophosphamide, FK-506, rapamycin and corticosteroids. Agents finding increased use in immunosuppressive therapy due to their preferential effect on T-cell mediated reactions are the cyclosporins.

Following transplantation, administration of the immunosuppressive agent must be continued indefinitely since the benefits of immunosuppressive therapy are reversible and graft rejection may occur once administration of the immunosuppressive agent is discontinued. While use of immunosuppressive agents, such as Cyclosporin A, has been reported to prolong the survival of allogeneic transplants involving skin, heart, kidney, pancreas, bone marrow, small intestine and lung, use of such agents is not without undesirable side effects. Examples of undesirable side effects include increased risk of development of neoplastic disease conditions, e.g., skin cancer, lymphoma, etc.

While most recipients who discontinue their immunosuppressive treatment following a graft go on to suffer rejection, not all subjects suffer graft rejection. In a few cases, individuals tolerate their graft without immunosuppression, suggesting that immune non-responsiveness can be achieved in clinical practice. The mechanisms of this process are not well understood, but may involve a combination of clonal deletion, clonal anergy and the generation of active regulatory T cells.

Because of the undesirable sides effects and risks of long term immunosuppressive therapy, it would be desirable to be able identify those individuals who are tolerant to their graft, i.e., graft tolerant, so that immunosuppression could be reduced or even discontinued in those individuals. Of particular interest would be the development of a way to identify graft tolerant individuals without first discontinuing immunosuppressive therapy, thereby avoiding the risk of graft rejection and damage to the graft associated therewith. The present invention meets this need.

RELEVANT LITERATURE

Publications of interest include: United States Patent Application No. 2003/0104371.

SUMMARY OF THE INVENTION

Methods are provided for determining whether a subject has a graft tolerant phenotype. In practicing the subject methods, the expression of at least one gene in a sample from the subject, e.g., a blood sample, is assayed to obtain an expression evaluation for the at least one gene. The obtained expression evaluation is then employed to determine whether the subject has a graft tolerant phenotype. Also provided are compositions, systems and kits that find use in practicing the subject methods. The subject methods and compositions find use in a variety of applications, including the determination of an immunosuppressive therapy regimen.

The subject invention provides methods of determining whether a subject has a graft tolerant phenotype, where the methods include: evaluating expression of at least one gene in a sample from the subject to determine whether the subject has a graft tolerant phenotype. In certain embodiments, the expression of at least one gene is evaluated by assaying the sample for a nucleic acid transcript of the gene. In certain embodiments, the expression of at least one gene is evaluated by assaying the sample for an expression product of the gene. In certain embodiments, the sample is a blood sample. In certain embodiments, the blood sample is a peripheral blood sample. In certain embodiments, the at least one gene is a gene listed on Tables 1, 2, 3 and/or 4. In certain embodiments, expression of at least 5 genes from Tables 1, 2, 3 and/or 4 is evaluated. In certain embodiments, expression of at least 50 genes from Tables 1, 2, 3 and/or 4 is evaluated.

Also provided are methods of determining whether a subject has a graft tolerant phenotype by: (a) obtaining an expression profile for a sample from the subject; and (b) employing the obtained expression profile to determine whether the subject has a graft tolerant phenotype. In certain embodiments, the expression profile is compared to a reference expression profile in the employing step (b). In certain embodiments, the reference expression profile is a graft tolerant phenotype expression profile. In certain embodiments, the reference expression profile is a graft intolerant phenotype expression profile. In certain embodiments, the expression profile comprises expression measurements for at least 5 different genes. In certain embodiments, the at least 5 different genes are listed in Tables 1, 2, 3 and/or 4. In certain embodiments, the expression profile is determined using a microarray. In certain embodiments, the microarray is a genomic array. In certain embodiments, the microarray is a proteomic array.

Also provided is a method of managing immunosuppressive therapy in a subject having a graft, where the method includes: (a) evaluating whether the subject has an graft tolerant phenotype; and (b) determining a future immunosuppressive therapy protocol based on the evaluation of step (a) to manage immunosuppressive therapy in said subject. In certain embodiments, the evaluating step (a) is by a method as described above. In certain embodiments, the method comprises at least reducing immunosuppression in the subject if said subject is found to have a graft tolerant phenotype. In certain embodiments, the method comprises discontinuing immunosuppression in the subject if the subject is found to have a graft tolerant phenotype.

Also provided are systems for determining whether a subject has an graft tolerant phenotype, where the systems include: (a) a gene expression evaluation element for evaluating expression of at least one gene in a sample to obtain a gene expression result; and (b) a phenotype determination element for employing the gene expression result to determine whether a subject has a graft tolerant phenotype. In certain embodiments, the gene expression evaluation element comprises at least one reagent for assaying a sample for a nucleic acid transcript of said gene. In certain embodiments, the gene expression evaluation element comprises at least one reagent for assaying a sample for an expression product of said gene. In certain embodiments, the gene expression evaluation element comprises an array. In certain embodiments, the at least one gene is a gene listed in Tables 1, 2, 3 and/or 4. In certain embodiments, the phenotype determination element comprises a reference expression value for the at least one gene. In certain embodiments, the phenotype determination element comprises a reference expression profile that includes a reference expression value for at least one additional gene. In certain embodiments, the reference expression profile is a graft tolerant phenotype expression profile. In certain embodiments, the reference expression profile is a graft intolerant phenotype expression profile.

Also provided are kits for determining whether a subject has a graft tolerant phenotype, where the kits include: (a) a gene expression evaluation element for evaluating expression of at least one gene in a sample to obtain a gene expression result; (b) a phenotype determination element for employing the gene expression result to determine whether a subject has a graft tolerant phenotype; and (c) instructions for using said gene expression evaluation and phenotype determination elements in a method, e.g., as described above. In certain embodiments, the gene expression evaluation element comprises at least one reagent for assaying a sample for a nucleic acid transcript of said gene. In certain embodiments, the gene expression evaluation element comprises at least one reagent for assaying a sample for an expression product of said gene. In certain embodiments, the gene expression evaluation element comprises an array. In certain embodiments, the at least one gene is a gene listed in Tables 1, 2, 3 and/or 4. In certain embodiments, the phenotype determination element comprises a reference expression value for the at least one gene. In certain embodiments, the phenotype determination element comprises a reference expression profile that includes a reference expression value for at least one additional gene. In certain embodiments, the reference expression profile is a graft tolerant phenotype expression profile. In certain embodiments, the reference expression profile is a graft intolerant phenotype expression profile. Also provided are reference expression profiles for a phenotype that is one of: (a) graft tolerant; or (b) graft intolerant; wherein the expression profile is recorded on a computer readable medium. In certain embodiments, the expression profile includes at least one of the genes from Tables 1, 2, 3 and/or 4. In certain embodiments, the expression profile is a profile for a phenotype that is allograft tolerant. In certain embodiments, the expression profile is a profile for a phenotype that is graft intolerant.

Also provide by the invention is a collection of reagents for evaluating gene expression, where the collection includes: reagents specific for at least two of the genes of Tables 1, 2, 3 and/or 4. In certain embodiments, the reagents are gene specific primers. In certain embodiments, the collection comprises at least 10 gene specific primers.

Also provided are arrays of probe nucleic acids immobilized on a solid support, where the arrays include: a plurality of probe nucleic acid compositions, wherein each probe nucleic acid composition is specific for a gene whose expression profile is indicative of a graft tolerance, wherein at least two of the probe nucleic acid compositions correspond to genes listed in Tables 1, 2, 3 and/or 4.

Also provided are kits that include at least one of (a) an array according as described above; and (b) a collection of gene specific primers as described above, where in certain embodiments the kits include both of these components.

BRIEF DESCRIPTION OF THE FIGURES

FIG. 1 provides Table 1, which lists 200 representative genes whose expression differs in OT patients relative to those with chronic graft injury.

FIG. 2 provides Table 2, which is an analysis of 591 genes differentially expressed in PBL samples associated with tolerance in renal transplantation.

FIG. 3 provides Table 3, which shows the gene expression differences between OT and CR samples by KEGG families.

DESCRIPTION OF THE SPECIFIC EMBODIMENTS

Methods are provided for determining whether a subject has a graft tolerant phenotype. In practicing the subject methods, the expression of at least one gene in a sample from the subject, e.g., a blood sample, is assayed to obtain an expression evaluation for the at least one gene. The obtained expression evaluation is then employed to determine whether the subject has a graft tolerant phenotype. Also provided are compositions, systems and kits that find use in practicing the subject methods. The methods and compositions find use in a variety of applications, including the determination of an immunosuppressive therapy regimen.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As summarized above, the subject invention is directed to methods of determining whether a subject has a graft tolerant phenotype, as well as reagents and kits for use in practicing the subject methods. In further describing the invention, the subject methods are described first, followed by a review of the reagents and kits for use in practicing the subject methods.

Methods of Determining Whether a Subject has a Graft Tolerant Phenotype

The subject invention provides methods of determining whether a patient or subject has a graft tolerant phenotype. By graft tolerant phenotype is meant that the subject does not reject a graft organ, tissue or cell(s) that has been introduced into/onto the subject. In other words, the subject tolerates or maintains the organ, tissue or cell(s) that has been transplanted to it. As in known in the transplantation field, the graft organ, tissue or cell(s) may be allogeneic or xenogeneic, such that the grafts may be allografts or xenografts. A feature of the graft tolerant phenotype detected or identified by the subject methods is that it is a phenotype which occurs without immunosuppressive therapy, i.e., it is present in a host that is not undergoing immunosuppressive therapy such that immunosuppressive agents are not being administered to the host.

In practicing the subject methods, a subject or patient sample, e.g., cells or collections thereof, e.g., tissues, is assayed to determine whether the host from which the assayed sample was obtained is graft tolerant, i.e., has a graft tolerant phenotype. Accordingly, the first step of the subject methods is to obtain a suitable sample from the subject or patient of interest, i.e., a patient on immunosuppressive therapy and having at least one graft, e.g., allograft. The sample is derived from any initial suitable source, where sample sources of interest include, but are not limited to, many different physiological sources, e.g., CSF, urine, saliva, tears, tissue derived samples, e.g., homogenates, and blood or derivatives thereof.

In certain embodiments, a suitable initial source for the patient sample is blood. As such, the sample employed in the subject assays of these embodiments is generally a blood-derived sample. The blood derived sample may be derived from whole blood or a fraction thereof, e.g., serum, plasma, etc., where in many embodiments the sample is derived from blood cells harvested from whole blood. Of particular interest as a sample source are peripheral blood lymphocytes (PBL). Any convenient protocol for obtaining such samples may be employed, where suitable protocols are well known in the art.

In practicing the subject methods, the sample is assayed to obtain an expression evaluation, e.g., expression profile, for one or more genes, where the term expression profile is used broadly to include a genomic expression profile, e.g., an expression profile of nucleic acid transcripts, e.g., mRNAs, of the one or more genes of interest, or a proteomic expression profile, e.g., an expression profile of one or more different proteins, where the proteins/polypeptides are expression products of the one or more genes of interest. As such, in certain embodiments the expression of only one gene is evaluated. In yet other embodiments, the expression of two or more, e.g., about 5 or more, about 10 or more, about 15 or more, about 25 or more, about 50 or more, about 100 or more, about 200 or more, etc., genes is evaluated. Accordingly, in the subject methods, the expression of at least one gene in a sample is evaluated. In certain embodiments, the evaluation that is made may be viewed as an evaluation of the transcriptosome, as that term is employed in the art. See e.g., Gomes et al., Blood (2001 Jul. 1) 98(1):93-9.

In generating the expression profile, in many embodiments a sample is assayed to generate an expression profile that includes expression data for at least one gene/protein, usually a plurality of genes/proteins, where by plurality is meant at least two different genes/proteins, and often at least about 5, typically at least about 10 and more usually at least about 20 different genes/proteins or more, such as 50 or more, 100 or more, etc.

In the broadest sense, the expression evaluation may be qualitative or quantitative. As such, where detection is qualitative, the methods provide a reading or evaluation, e.g., assessment, of whether or not the target analyte, e.g., nucleic acid or expression product, is present in the sample being assayed. In yet other embodiments, the methods provide a quantitative detection of whether the target analyte is present in the sample being assayed, i.e., an evaluation or assessment of the actual amount or relative abundance of the target analyte, e.g., nucleic acid in the sample being assayed. In such embodiments, the quantitative detection may be absolute or, if the method is a method of detecting two or more different analytes, e.g., target nucleic acids, in a sample, relative. As such, the term "quantifying" when used in the context of quantifying a target analyte, e.g., nucleic acid(s), in a sample can refer to absolute or to relative quantification. Absolute quantification may be accomplished by inclusion of known concentration(s) of one or more control analytes and referencing the detected level of the target analyte with the known control analytes (e.g., through generation of a standard curve). Alternatively, relative quantification can be accomplished by comparison of detected levels or amounts between two or more different target analytes to provide a relative quantification of each of the two or more different analytes, e.g., relative to each other.

Genes/proteins of interest are genes/proteins that are differentially expressed or present at different levels in graft tolerant and graft intolerant individuals. Representative genes/proteins of interest in certain embodiments include, but are not limited to, the genes/proteins provided in Table 1. (Note that for Table 1, the exact sequence of the clone identified in the table can be determined through the NCBI Entrez nucleotide database at located at the website produced by placing "http://www." before: "ncbi.nlm.nih.gov/entrez/query.fcgi?CMD=search&db=nucleotide"; the sequence for a specific clone is then obtained by entering the clone ID in quotes as the search term).

In certain embodiments, at least one of the genes/proteins in the prepared expression profile is from Tables 1, 2, 3 and/or 4, where the expression profile may include expression data for 5, 10, 20, 50, 75 or more of, including all of, the genes/proteins listed in Tables 1, 2, 3 and/or 4. The number of different genes/proteins whose expression and/or quantity data, i.e., presence or absence of expression, as well as expression/quantity level, that are included in the expression profile that is generated may vary, but may be at least 2, and in many embodiments ranges from 2 to about 100 or more, sometimes from 3 to about 75 or more, including from about 4 to about 70 or more.

In certain embodiments, the expression profile obtained is a genomic or nucleic acid expression profile, where the amount or level of one or more nucleic acids in the sample is determined, e.g., the nucleic acid transcript of the gene of interest. In these embodiments, the sample that is assayed to generate the expression profile employed in the diagnostic methods is one that is a nucleic acid sample. The nucleic acid sample includes a plurality or population of distinct nucleic acids that includes the expression information of the phenotype determinative genes of interest of the cell or tissue being diagnosed. The nucleic acid may include RNA or DNA nucleic acids, e.g., mRNA, cRNA, cDNA etc., so long as the sample retains the expression information of the host cell or tissue from which it is obtained. The sample may be prepared in a number of different ways, as is known in the art, e.g., by mRNA isolation from a cell, where the isolated mRNA is used as is, amplified, employed to prepare cDNA, cRNA, etc., as is known in the differential expression art. The sample is typically prepared from a cell or tissue harvested from a subject to be diagnosed, e.g., via biopsy of tissue, using standard protocols, where cell types or tissues from which such nucleic acids may be generated include any tissue in which the expression pattern of the to be determined phenotype exists, including, but not limited to, peripheral blood lymphocyte cells, etc, as reviewed above.

The expression profile may be generated from the initial nucleic acid sample using any convenient protocol. While a variety of different manners of generating expression profiles are known, such as those employed in the field of differential gene expression analysis, one representative and convenient type of protocol for generating expression profiles is array-based gene expression profile generation protocols. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions; whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions, and unbound nucleic acid is then removed.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

"Stringent hybridization conditions" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions which determine whether a nucleic acid is specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1× SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

The resultant pattern of hybridized nucleic acid provides information regarding expression for each of the genes that have been probed, where the expression information is in terms of whether or not the gene is expressed and, typically, at what level, where the expression data, i.e., expression profile (e.g., In the form of a transcriptosome), may be both qualitative and quantitative.

Alternatively, non-array based methods for quantitating the levels of one or more nucleic acids in a sample may be employed, including quantitative PCR, and the like.

Where the expression profile is a protein expression profile, any convenient protein quantitation protocol may be employed, where the levels of one or more proteins in the assayed sample are determined. Representative methods include, but are not limited to: proteomic arrays, flow cytometry, standard immunoassays (e.g., ELISA assays), etc.

Following obtainment of the expression profile from the sample being assayed, the expression profile is compared with a reference or control profile to determine the particular graft tolerant/intolerant phenotype of the cell or tissue, and therefore host, from which the sample was obtained/derived. The terms "reference" and "control" as used herein mean a standardized pattern of gene expression or levels of expression of certain genes to be used to interpret the expression signature of a given patient and assign a graft tolerant/intolerant phenotype thereto. The reference or control profile may be a profile that is obtained from a cell/tissue known to have the desired phenotype, e.g., tolerant phenotype, and therefore may be a positive reference or control profile. In addition, the reference/control profile may be from a cell/tissue known to not have the desired phenotype, e.g., an intolerant phenotype, and therefore be a negative reference/control profile.

In certain embodiments, the obtained expression profile is compared to a single reference/control profile to obtain information regarding the phenotype of the cell/tissue being assayed. In yet other embodiments, the obtained expression profile is compared to two or more different reference/control profiles to obtain more in depth information regarding the phenotype of the assayed cell/tissue. For example, the obtained expression profile may be compared to a positive and negative reference profile to obtain confirmed information regarding whether the cell/tissue has the phenotype of interest.

The comparison of the obtained expression profile and the one or more reference/control profiles may be performed using any convenient methodology, where a variety of methodologies are known to those of skill in the array art, e.g., by comparing digital images of the expression profiles, by comparing databases of expression data, etc. Patents describing ways of comparing expression profiles include, but are not limited to, U.S. Pat. Nos. 6,308,170 and 6,228,575, the disclosures of which are herein incorporated by reference. Methods of comparing expression profiles are also described above.

The comparison step results in information regarding how similar or dissimilar the obtained expression profile is to the control/reference profile(s), which similarity/dissimilarity information is employed to determine the phenotype of the cell/tissue being assayed. For example, similarity with a positive control indicates that the assayed cell/tissue has a tolerant phenotype. Likewise, similarity with a negative control indicates that the assayed cell/tissue has an intolerant phenotype.

Depending on the type and nature of the reference/control profile(s) to which the obtained expression profile is compared, the above comparison step yields a variety of different types of information regarding the cell/tissue that is assayed. As such, the above comparison step can yield a positive/negative determination of a tolerant phenotype of an assayed cell/tissue. In many embodiments, the above-obtained information about the cell/tissue being assayed is employed to diagnose a host, subject or patient with respect to that host's graft tolerance, as described above.

The subject methods further find use in pharmacogenomic applications. In these applications, a subject/host/patient is first diagnosed for the presence of absence of the graft tolerant phenotype using a protocol such as the diagnostic protocol described in the preceding section. The subject is then treated using a protocol whose suitability is determined using the results of the diagnosis step. More specifically, where the identified phenotype is tolerant, a protocol that may include a reduced level of immunosuppression (i.e., immunosuppression at a level less than that which is indicated for patients not known to be graft tolerant), or no immunosuppression, may be employed to manage/treat the subject. Alternatively, where a patient is identified as having an intolerant phenotype, full immunosuppressive protocols are then employed/continued.

In many embodiments, a host is screened for the presence of a graft tolerant phenotype following receipt of a graft or transplant. The host may be screened once or serially following transplant receipt, e.g., weekly, monthly, bimonthly, half-yearly, yearly, etc., as long as the host is on immunosuppressive therapy. In certain embodiments, monitoring of the host expression profile even after immunosuppressive therapy has been reduced or discontinued is conducted to determine whether the host has maintained the tolerogenic expression profile and may continue for the lifetime of the host.

Databases of Expression Profiles of Phenotype Determinative Genes

Also provided are databases of expression profiles of graft tolerant phenotype determinative genes. Such databases will typically comprise expression profiles of various cells/tissues having graft tolerant phenotypes, negative expression profiles, etc., where such profiles are further described below.

The expression profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. One format for an output means ranks expression profiles possessing varying degrees of similarity to a reference expression profile. Such presentation provides a skilled artisan with a ranking of similarities and identifies the degree of similarity contained in the test expression profile.

Reagents and Kits

Also provided are reagents and kits thereof for practicing one or more of the above-described methods. The subject reagents and kits thereof may vary greatly. Reagents of interest include reagents specifically designed for use in production of the above-described expression profiles of phenotype determinative genes, i.e., a gene expression evaluation element made up of one or more reagents.

One type of such reagent is an array of probe nucleic acids in which the phenotype determinative genes of interest are represented. A variety of different array formats are known in the art, with a wide variety of different probe structures, substrate compositions and attachment technologies. Representative array structures of interest include those described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280.

In many embodiments, the arrays include probes for at least 1 of the genes listed in Tables 1, 2, 3 and/or 4. In certain embodiments, the number of genes that are from Tables 1, 2, 3 and/or 4 that is represented on the array is at least 5, at least 10, at least 25, at least 50, at least 75 or more, including all of the genes listed in Tables 1, 2, 3 and/or 4. The subject arrays may include only those genes that are listed in Tables 1, 2, 3 and/or 4, or they may include additional genes that are not listed in Tables 1, 2, 3 and/or 4. Where the subject arrays include probes for such additional genes, in certain embodiments the number % of additional genes that are represented does not exceed about 50%, usually does not exceed about 25%. In many embodiments where additional "non-Table 1" genes are included, a great majority of genes in the collection are phenotype determinative genes, where by great majority is meant at least about 75%, usually at least about 80% and sometimes at least about 85, 90, 95% or higher, including embodiments where 100% of the genes in the collection are phenotype determinative genes.

Another type of reagent that is specifically tailored for generating expression profiles of phenotype determinative genes is a collection of gene specific primers that is designed to selectively amplify such genes. Gene specific primers and methods for using the same are described in U.S. Pat. No. 5,994,076, the disclosure of which is herein incorporated by reference. Of particular interest are collections of gene specific primers that have primers for at least 1 of the genes listed in one Tables 1, 2, 3 and/or 4, often a plurality of these genes, e.g., at least 2, 5, 10, 15 or more. In certain embodiments, the number of genes that are from Tables 1, 2, 3 and/or 4 that have primers in the collection is at least 5, at least 10, at least 25, at least 50, at least 75 or more, including all of the genes listed in Tables 1, 2, 3 and/or 4. The subject gene specific primer collections may include only those genes that are listed in Tables 1, 2, 3 and/or 4, or they may include primers for additional genes that are not listed in Tables 1, 2, 3 and/or 4. Where the subject gene specific primer collections include primers for such additional genes, in certain embodiments the number % of additional genes that are represented does not exceed about 50%, usually does not exceed about 25%. In many embodiments where additional "non-Table 1", "non-Table 2", "non-Table 3" or "non-Table 4" genes are included, a great majority of genes in the collection are phenotype determinative genes, where by great majority is meant at least about 75%, usually at least about 80% and sometimes at least about 85, 90, 95% or higher, including embodiments where 100% of the genes in the collection are phenotype determinative genes.

The kits of the subject invention may include the above-described arrays and/or gene specific primer collections. The kits may further include one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

The subject kits may also include a phenotype determination element, which element is, in many embodiments, a reference or control expression profile that can be employed, e.g., by a suitable computing means, to make a phenotype determination based on an "input" expression profile, e.g., that has been determined with the above described gene expression evaluation element. Representative phenotype determination elements include databases of expression profiles, e.g., reference or control profiles, as described above.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Systems

Also provided are systems for practicing one or more of the above-described methods. The subject systems may vary greatly, but typically include at least a gene expression evaluation element, e.g., one or more reagents, and a phenotype determination element.

Reagents of interest include reagents specifically designed for use in production of the above-described expression profiles of phenotype determinative genes, i.e., a gene expression evaluation element made up of one or more reagents. One type of such reagent is an array of probe nucleic acids in which the phenotype determinative genes of interest are represented. A variety of different array formats are known in the art, with a wide variety of different probe structures, substrate compositions and attachment technologies. Representative array structures of interest include those described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280.

In many embodiments, the arrays include probes for at least 1 of the genes listed in Tables 1, 2, 3 and/or 4. In certain embodiments, the number of genes that are from Tables 1, 2, 3 and/or 4 that is represented on the array is at least 5, at least 10, at least 25, at least 50, at least 75 or more, including all of the genes listed in Tables 1, 2, 3 and/or 4. The subject arrays may include only those genes that are listed in Tables 1, 2, 3 and/or 4, or they may include additional genes that are not listed in Tables 1, 2, 3 and/or 4. Where the subject arrays include probes for such additional genes, in certain embodiments the number % of additional genes that are represented does not exceed about 50%, usually does not exceed about 25%. In many embodiments where additional "non-Table 1", "non-Table 2", "non-Table 3" or "non-Table 4" genes are included, a great majority of genes in the collection are phenotype determinative genes, where by great majority is meant at least about 75%, usually at least about 80% and sometimes at least about 85, 90, 95% or higher, including embodiments where 100% of the genes in the collection are phenotype determinative genes.

Another type of reagent that is specifically tailored for generating expression profiles of phenotype determinative genes is a collection of gene specific primers that is designed to selectively amplify such genes. Gene specific primers and methods for using the same are described in U.S. Pat. No. 5,994,076, the disclosure of which is herein incorporated by reference. Of particular interest are collections of gene specific primers that have primers for at least 1 of the genes listed in one Tables 1, 2, 3 and/or 4, often a plurality of these genes, e.g., at least 2, 5, 10, 15 or more. In certain embodiments, the number of genes that are from Tables 1, 2, 3 and/or 4 that have primers in the collection is at least 5, at least 10, at least 25, at least 50, at least 75 or more, including all of the genes listed in Tables 1, 2, 3 and/or 4. The subject gene specific primer collections may include only those genes that are listed in Tables 1, 2, 3 and/or 4, or they may include primers for additional genes that are not listed in Tables 1, 2, 3 and/or 4. Where the subject gene specific primer collections include primers for such additional genes, in certain embodiments the number % of additional genes that are represented does not exceed about 50%, usually does not exceed about 25%. In many embodiments where additional "non-Table 1", "non-Table 2", "non-Table 3" or "non-Table 4" genes are included, a great majority of genes in the collection are phenotype determinative genes, where by great majority is meant at least about 75%, usually at least about 80% and sometimes at least about 85, 90, 95% or higher, including embodiments where 100% of the genes in the collection are phenotype determinative genes.

The systems of the subject invention may include the above-described arrays and/or gene specific primer collections. The systems may further include one or more additional reagents employed in the various methods, such as primers for generating target nucleic adds, dNTPs and/or rNTPs which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

The systems may also include a phenotype determination element, which element is, in many embodiments, a reference or control expression profile that can be employed, e.g., by a suitable computing means, to make a phenotype determination based on an "input" expression profile, e.g., that has been determined with the above described gene expression evaluation element. Representative phenotype determination elements include databases of expression profiles, e.g., reference or control profiles, as described above.

The following examples are offered by way of illustration and not by way of limitation.

EXPERIMENTAL

I. Methods and Materials

Patient Selection

The protocol was accepted by the University Hospital Ethical Committee and the Committee for the Protection of Patients from Biological Risks. All patients and normal individuals were informed of the protocol and signed an informed consent. IRB approval was also obtained to perform DNA microarrays on all patient samples at Stanford University. The 42 adult participants in this study were classified into four groups for comparison: operationally tolerant (OT), chronic rejection (CR), stable, or normal.

Operationally tolerant patients were kidney graft recipients with stable graft function who had not taken any immunosuppressive drugs for at least three years (N=5) with a mean drug free time period was 8±3.3 years [range 3-12]. Eleven additional patients who received low doses (≤10 mg/day) of Prednisone® or Cortancyl® as the only immunosuppressive drug for at least 3 years before analysis were also classified Op-Tol (or OT). The mean time period of immunosuppression was 9.8±4.4 years [range 4-15]. The renal function of drug-free tolerant patients and minimally immunosuppressed patients remained stable and blood creatinemia was not significantly different before and after immunosuppression interruption or modification.

Patients with chronic rejection, patients with stable function under immunosuppressive maintenance regimen and normal healthy individuals are used as control groups. The chronic rejection group included patients with histological chronic rejection lesions (CR group) associated or not to an allograft glomerulopathy and with a degradation of their renal function. Inclusion was evidenced by clinical indices indicative of end-stage renal disease requiring hemodialysis (N=3) or serum creatine and proteinuria >1.5 g/day and creatinemia >60 μmol and by evidence of rejection on kidney biopsies. The stable function group included patients with stable graft function and under a bitherapy immunosuppressive regimen including a calcineurin inhibitor (StaCNI+) or not (StaCNI−). The inclusion of patients with stable function under standard IS required all following criteria: a) Patients over 18 years old; b) received kidney transplant between 5 to 8 years; c) patients without acute rejection history; d) patients with good immunosuppressive treatment compliance (as judged by medication intake and medical survey); e) patients under standard dual immunosuppressive maintenance treatment including: CsA or FK506 and mycophenolate mofetil, azathioprine or corticosteroids; f) stable kidney function (i.e. ±25% of the mean value of the year that preceded the test) and with a Nankivell calculated clearance (*please provide reference) above 40 ml/min after at least five year of transplantation and at one and three months after the inclusion in the study; g) proteinuria <1.5 g/day and creatinemia<160 umol after at least five year of transplantation and at one and three months after the inclusion in the study; h) blood trough-levels within the International standard range (75-250 ng/ml) for Neoral and 5-10 ng/ml for Prograf). Normal individuals included healthy individuals were 25 to 60 years old (N=3) with a normal blood formula and no known infectious pathology for at least 6 months prior to the study.

RNA Extraction from Whole Samples

Blood, harvested in EDTA tubes, was obtained from a peripheral vein or arterio-venous fistula. Ionogramm, WBC, formula and CNI blood levels (RIA) were performed on each sample. Peripheral blood leukocytes (PBL) were separated on a Ficoll layer (Eurobio, Les Ulis, France) and frozen in Trizol reagent (Invitrogen, Life Technologies, San Diego, Calif.) for RNA extraction.

Microarray Hybridization and Data Analysis

The cDNA microarrays were processed using protocols as previously described by our laboratory using 2 μg RNA in each channel (Sarwal, et al., N. Engl. J. Med. (2003) 349: 125-138). A "common reference" RNA pool (Perou, et al., Nature (2000) 406:747-752) was used as an internal standard with each hybridization. Sample or reference RNA was subjected to two successive rounds of amplification before hybridization to the cDNA microarrays using a protocol essentially as described by Wang et al. (Wang, et al., Nat. Biotechn. (2000) 18:457-459). Hybridized microarrays were scanned using GenePix 4000 (Axon Instruments, Union City, Calif.) and fluorescent images were analyzed with the GenePix Pro software package. Each microarray contains approximately 30,000 cDNAs representing over 12,400 unique genes.

Array data for the 42 samples were stored in the Stanford Microarray database (Sherlock, et al., Nuc. Acids Res. (2001) 29:152-155) and gene lists filtered at retrieval. The hybridized raw data of 30,000 cDNA spots was manually examined for single spots or blemishes (Alizadeh et al., Cold Spring Harbor Symp. Quant. Biol. (1999) 64:71-78). These spots or belmishes were flagged and removed, generating a data file with 22,090 clones under low stringency (70% representative data and signal/noise ratio of expression measurements >1.5). Further high-stringency data filtering, choosing only clones with 90% representative data and a 4-fold expression level difference at >2 arrays in the study set generated a file of 2,083 cDNA clones representing 1,846 unique genes. This higher-stringency gene set was further analyzed for potential biomarkers in this study and in a study of the T-cell expression profiles from the same patient groups. Cluster (V3.0) generated hierarchical clusters of the samples measuring similarity of expression of the genes and similarity across arrays which are visualized with the TreeView program (Eisen et al., Proc. Nat'l Acad. Sci USA (1998) 95:14863-8; (See also the website found by positioning "http://www." in front of "microarrays.org/software." Significance of gene expression differences among the groups of samples was performed using Statistical Analysis of Microarray (SAM) (Tusher et al., Proc. Nat'l Acad. Sci USA (2001) 98:5116-21) using a false discovery rate threshold of <5%.

Taqman-Based Quantitative RT-PCR

One hundred nanograms of amplified RNA were subjected to real-time PCR analysis to assess quantization of marker genes identified in the microarray screen. Assay-on-demand primer sets and Taqman EZ RT-PCR core reagents (Applied Biosystems, Foster City, Calif.) were used according to manufacturers directions in 20 μL reaction volumes using the 7900HT Sequence Detection System. Transcript levels were calculated according to the 2-ΔΔCt method of the manufacturer (1997). The labeled TaqMan® probes (Assays-on-demand, Applied Biosystems) used for these assays include:

```
                                                (SEQ ID NO: 01)
β-Actin: 5'FAM-TCGCCTTTGCCGATCCGCCGCCCGT-NFQ3';

(SEQ ID NO: 02)
TK1:    5'FAM-ACACATGACCGGAACACCATGGAGG-NFQ3';

(SEQ ID NO: 03)
C1S:    5'FAM-TTGCCACAGACATAAATGAATGCAC-NFQ3';

(SEQ ID NO: 04)
EV12A:  5'FAM-AAGCATTTTGTAAGATTGCCAAGTA-NFQ3';

(SEQ ID NO: 05)
MMP2:   5'FAM-GCAGGGCGGCGGTCACAGCTACTTC-NFQ3';

(SEQ ID NO: 06)
MAPK9:  5'FAM-GATTGTTTGTGCTGCATTTGATACA-NFQ3';

(SEQ ID NO: 07)
TCEB3:  5'FAM-AGACATTCTTGCGGAGACTGGGGTT-NFQ3';

(SEQ ID NO: 08)
KIFC3:  5'FAM-CAAGGCCGAGATAGGCCAGGCCATC-NFQ3';

(SEQ ID NO: 09)
PRAME:  5'FAM-CGTTTGTGGGGTTCCATTCAGAGCC-NFQ3';

(SEQ ID NO: 10)
DLK1:   5'FAM-GATCAACGGCTCCCCCTGCCAGCAC-NFQ3';

(SEQ ID NO: 11)
CYR61:  5'FAM-CTGCAGAGCTCAGTCAGAGGGCAGA-NFQ3';

(SEQ ID NO: 12)
HPRT:   5'FAM-GGTCAAGGTCGCAAGCTTGCTGGTG-NFQ3';

(SEQ ID NO: 13)
GAPDH:  5'FAM-GGGCGCCTGGTCACCAGGGCTGCTT-NFQ3'.
```

II. Results

We compared gene expression profiles from RNA extracted using unfractionated peripheral blood samples from 16 operationally tolerant (OT) patients (4 without any treatment, 12 with low dose steroid monotherapy) with that from 11 patients with signs of chronic rejection (CR), 12 transplant patients with stable function (S), and from three normal controls (N; healthy un-grafted individuals). Unsupervised analysis revealed that the majority of the CR and OT samples segregate into separate groups. In addition, all of the normal samples and most of the stable samples were observed to cluster with the CR patient groups. A recent reference study of whole gene expression profiling using the same cDNA array platform employed in this study, Whitney et al. (Whitney et al., Proc. Nat'l Acad. Sci. USA (2003) 100:1896-901) made at least two key discoveries that assisted in the interpretation of our expression results. First, blood-based gene expression profiles from the same individual were quite stable over time; second, genes from a common cell origin in PBL samples tend to tightly cluster as evidenced by correlation analysis between cell counts and expression measurements.

Separation of the sample groups was primarily driven by three gene clusters identified as A, B and C with a large percentage of the genes expressed at higher levels in the blood from OT patients than others. By identifying cell signaling genes tightly clustered to ones of limited tissue expression, one can then infer the putative cell origin, and immune activation status of the primary clusters. In addition, genes might be highly differentially expressed between the two phenotypes of interest, OT and CR in this study.

Because the OT and CR patients largely group into separate branches in the unsupervised expression analysis, close examination of the observed gene clusters provided insight into potential functional roles for the major genes involved in the tolerance signature. Both pro- and anti-apoptotic genes were identified as highly differentially expressed between OT and CR patients. Expression patterns of the anti-apoptotic genes TOSO, CASP7 and FIAM2 in Cluster A parallel both T- and B-cell specific genes including the T-cell receptor (TCR), HLA class II genes, several immunoglobulin genes (IGL, IG1L1, IGJ3, IGHM). This cluster also contained a number of key cytokines that play a role in the immune signaling: (CCL20, CCL19, CCL8 and CCR7). This cluster also contained the T-cell activation antigen CD27, which serves as a regulator of B-cell activation is the receptor for the pro-apoptotic CD27-binding protein (SIVA). In contrast, the pro-apoptosis genes RGN and RIS1 co-clustered with platelet and T-suppressor cell specific genes CD9 and GFBB2 respectively. It is this cluster, Cluster C, which contained a number of immune response genes (C1s, IER3, and CD59) and several cell cycle regulated genes (TK1, CCNA2, CDC20, CCND2, CCNA2, CCND1, MCM2 and CDC6) and GAGE4, an antigen of unknown function that is recognized by cytotoxic T-cells. IER3 (intermediate early response 3) functions to protect cells from Fas- or tumor necrosis factor (TNFα)-induced apoptosis. CD59, also known as protectin (MIC1), functions to restrict lysis of erythrocytes and leukocytes by homologous complement and is involved in signal transduction for T-cell activation. CD59 interacts with T-cell surface antigen CD2, a gene also highly differentially expressed in this dataset and found to co-cluster in Cluster B with NK4, CD5, CD6, CD81, CD8A, granulysin, and granzyme C and B. Additional NK-specific genes segregated with this gene group include NKG7 and ICAM3. Thus, both cytotoxic T-cell antigens and NK-cell specific genes are expressed in parallel and characterized this cluster. The NK-cell specific cluster also had elevated expression of IL-2 regulated genes including CTSW. Together, the expression data shows that at least 3 populations of circulating leukocytes are involved in the tolerance signature identified: increased expression of T- and B-cell genes and anti-apoptotic genes serving a protective role (Cluster A); T-cells expression NK antigens with elevated expression of NK4, NKG7 and cytotoxic signaling chemokines (Cluster B); and a rapidly proliferating platelet or suppressor T-cell population modulated by the pro-apoptotic genes RGN and RIS1 (Cluster C).

Supervised Statistical Analysis of the Expression Profiles

Of the 2,083 highly differentially expressed genes in this study, 550 were found to show significant differences in expression between the OT and CR patient groups using the SAM statistical analysis tool (Tusher, et al. supra) (q<5%). In contrast, no significant differences were observed within the 4 tolerant patients comparing those without any immunosuppressive drug vs. 12 tolerant patients under minimal immunosuppression (steroid monotherapy) (minimum false discovery rate >16%). This observation showed that the expression patterns were sufficiently similar to group all the tolerant patients together in class prediction analysis and collectively consider them "operationally tolerant". Far more up-regulated genes are evident in the genes highly correlated with the OT phenotype: 523 genes were up-regulated and only 27 down-regulated and these genes clustered the patient groups in a similar manner as the unsupervised analysis. This observation showed that the state of operational tolerance in these patients is not a passive process but is actively regulated. Further, the expression profiles showed that the state of operational tolerance involves active transcription across several hundred genes in concert in peripheral blood cells. This mechanism is consistent with the observation that a much larger number of differentially expressed genes were initially identified using the SAM analysis tool when 22,897 clones were retrieved from the SMD database with stringency filtering (70% representative data and signal/noise ratio >1.5). From this larger gene set, a total of 3,125 cDNA clones representing ~1,820 genes were identified in the full gene list with SAM significance score <5% (data not shown).

To identify genes whose expression differed in OT and CR patients from healthy control individuals, each gene was zero transformed to the average expression level in the 3 normal PBL samples and supervised analysis with SAM repeated. In this normalized dataset, 591 significant genes were identified, all of which are at higher levels in the OT samples than CR (clustered data not shown).

The differentially expressed genes that segregate the OT and CR patient groups include several interesting candidate genes involved in immune signaling cascades including specific transcription factors, cell adhesion molecules, cell cycle-specific genes, inhibitors of inflammation/alloresponse, growth factors, and genes with important roles in vascular biology. This subset is provided in Table 2. Each of these gene families are represented by multiple group members in the identified group of 591 significantly differentially expressed cDNAs as are B- and T-cell specific genes, apoptotic gene family members, protein kinases, several cell matrix/structural proteins as well as other functional categories. Expression fold differences between OT and CR patients of representative members of these gene families are summarized in Table 3. For the remainder of the study, we analyzed both the normalized data (zero transformed) and clustered data to identify putative biomarkers predictive of tolerance.

Class Prediction Analysis

PAM or Predictive Analysis of Microarray data (Tibshirani et al., Proc. Nat'l Acad. Sci. USA (2002) 99:6567-72) was used to identify those genes with highest predictive value in identifying a tolerogenic state in the blood samples. This program identifies a minimum gene set characteristic of user defined sample groups (the learning set) and then scores both known and unknown samples based on similarity to identified expression profile differences. Normalized expression ratios for OT and CR groups were used as a learning set and classification scores for the 12 stable patients determined by PAM analysis using threshold log-ratio difference of >1.5 (3-fold expression difference between OT and CR (Table 3). Although there was substantial overlap in the identified genes, the 30 top ranked genes from PAM class prediction analysis using zero-transformed data (and raw expression values) differ in how they cluster the samples. The latter dataset segregate OT and CR samples into separate branches that are in agreement with computed phenotype goodness-of-fit scores reported by the PAM class prediction program.

With the objective of further refining the gene set into a manageable number of genes for PCR-based analysis, the array data was analyzed by logistic regression. Class prediction using logistic regression modeling requires that markers independently correlate with the test phenotype which initially proved challenging with the array data due to the extremely tight clustering of many of the highest ranked genes. In all analysis performed, the expression of thymidine kinase 1 (TK1) showed the greatest difference comparing OT vs. CR (T-test p<0.00001) and highest expression in the tolerant patients. More importantly, the expression of several hundred genes positively correlated with TK1. For example, expression of 102 genes correlated with TK1 with $R^2 >0.7$ and 398 genes with $R^2 >0.5$ and, at least on the basis of the array data, these tightly correlating genes consistently had the highest significance scores. We therefore selected four candidate genes from the PAM class prediction set, two of which positively correlate with the tolerant phenotype (TK1 and C1s) and two of which negatively correlated (EV12A and MAPK9). Classification based on array data for these four genes give 95.8% concordant classification and 4.2% discordant classification within the test groups (Table 3). Remarkably, array-based expression ratios of TK1 alone yield 94.5% concordant classification and 4.2% discordant classification. In addition, the expression of TK1 also correlates with prediction scores generated by both PAM and logistic regression; $R^2 >0.85$ for logistic regression scores and $R^2 >0.80$ for PAM scores. Only 2 of the 39 samples classify discordantly between the two methods (5% discordance): Chronic patient #88 that PAM/microarray data profiles as consistent with the tolerant phenotype and Stable patient #89 which classifies as CR by PAM and OT by logistic regression. The overall expression profile of Stable patient #89 is sufficiently distinct from the tolerant patients that it fails to co-cluster with this group in all three sets of genes analyzed.

Confirmation of Gene Signature with Taqman PCR

Real-time quantitative RT-PCR was used to confirm expression difference between OT and CR patient groups using β-actin as a reference gene. RNA was available for this analysis from 8 of the OT patients, 11 CR patients and all 12 stable post-transplant patients and residual amplified cDNA prepared for the array expression study was used as the template source. In the small sample group analyzed, the expression of EV12A was the only gene tested to reach statistical significance. However, a significant correlation between array and PCR results were seen for EV12A, TK1 and C1s and average expression of MAPK9 was higher in the CR patients than OT, also in agreement with the array-based data. To determine whether all four markers combined would provide greater statistical power, logistic regression modeling was used to analyze the PCR data. The overall best the differentiation between OT and CR groups is obtained a cut-off of 0.02 using a curve described by the following algorithm (p<0.00005):

$$1/(1+\exp-[10.2373+17.2638(MPK9)+2.7098(EV12A)-4.8491(C1S)-10.1332(TK1)])$$

where gene names are the fold-difference measurements at each locus. The logistic regression model from these data had correct prediction of phenotype of 72.2% (sensitivity=75%, specificity=66.7%).

TK1 expression by quantitative RT-PCR was still the most informative of the genes in this analysis, although more inter-individual variation was observed in the Taqman results and hence this marker alone failed to reach the predictive power of the array data. However, we did find that the combined expression profiles of TK1, MAPK9, EV12A, and C1s, when analyzed by logistic regression, were in complete agreement with PAM prediction scoring of the OT and CR patients tested. One of the patients originally classified as tolerant at the time of the study (Patient #T/C04) was found to have evidence of chronic injury as evidenced by the detection of proteinuria. By including the data from this patient in the CR group of the learning set and repeating the analysis only using expression measurements on the TK1 locus, cutoffs at 0.10 and at 0.59 the logistic regression model have correct prediction probability of 83.3% (sensitivity 100%, specificity 50%) and 83.3% (sensitivity 91.7% and specificity 66.7%), respectively. Thus, a cutoff of 0.59 would maximize both the sensitivity and specificity in the classification by TK1 alone by logistic regression and this model also gave better fit than the 4-gene profile. However, agreement among the stable patients between the two test measures (PAM class prediction of global gene expression profiles vs. logistic regression analysis of RT-PCR data) was not as conclusive in that we found consistent classification between the two test methods in 9 of 12 stable patients (75%). Higher concordance within the OT and CR patients (100%) might be expected because these are the learning set in the analyses and the stable patients the test set (75% concordance). Together these data indicated that the blood-based expression signature of the tolerogenic state is subtle and a larger panel of genes, such as the 30 gene sets identified by PAM class prediction, may be beneficial in certain embodiments for accurate identification of the tolerance in a diagnostic setting.

Additional genes of interest are found in Table 4.

TABLE 4

| Accession | Gene | Description |
|---|---|---|
| NM_001003927 | EVI2A | ecotropic viral integration site 2A |
| NM_005601 | NKG7 | NATURAL KILLER CELL GROUP 7 SEQUENCE |
| M38690 | CD9 | LEUKOCYTE ANTIGEN MIC3 |
| U25931 | CD27 | TUMOR NECROSIS FACTOR RECEPTOR SUPERFAMILY |
| NM_014009 | FOXP3 | forkhead box P3 |
| NM_000953 | DP1 | prostaglandin D2 receptor |

III. Discussion and Conclusions

Identification of blood-based biomarkers with predictive power in directing clinical outcomes is an active area of clinical research. We used global gene expression monitoring to test whether blood-based markers diagnostic of spontaneously achieved tolerance could be identified in a cohort of long-term renal transplant patients. By normalizing to the average expression levels in normal control blood samples, several functional groups of genes were identified to be at significantly higher levels in the tolerant patients, where the identified genes included genes characteristic of rapid cell proliferation, anti-apoptotic activity and senescence, as well as genes involved in immune signaling cascades including specific transcription factors, cell adhesion molecules. Overall the data shows that the spontaneously achieved state of immune tolerance is an active regulatory process as evidenced by the large numbers of up-regulated genes relative to normal blood and by the highly synchronized expression signature that is observed. Further, this signature was observed in the blood from ~25% of long-term stable graft recipients showing that expression monitoring could become an invaluable method in realizing the goal of predictably reducing long-term immunosuppressive therapy when merited. The gene expression signatures were sufficiently strong that two independent classification methods, logistic regression and PAM analysis, gave similar predictive power (~90% overall) with differences in predicted phenotype for only 3 of 39 participants in this pilot study. Hierarchal clustering of the top 30 genes scored by PAM separated all patients classified tolerant and from those with chronic renal injury or graft rejection with 100% concordance to the logistic regression scoring. Identification of a large number of differentially expressed genes reported in this study of spontaneously tolerant adult renal transplant patients provides several biomarkers for spontaneously achieved immune tolerance. The gene expression study reported here shows that expression differences characteristic of spontaneously achieved tolerance can be detected in whole blood lysates obviating the need for more invasive methods of sampling.

It is evident that subject invention provides a convenient and effective way of determining whether a subject has a graft tolerant phenotype, without first removing the subject from immunosuppressive therapy. As such, the subject invention provides a number of distinct benefits, including the ability to easily identify subjects undergoing immunosuppressive therapy that have a graft tolerant phenotype, and therefore may be removed from immunosuppressive therapy, so that these individuals can avoid the adverse conditions, as well as costs, associated with such therapy. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for detecting a graft tolerant phenotype in a human subject, said method comprising:
   (a) assaying gene expression levels of chemokine (C-C motif) ligand 20 (CCL20), complement component 1s (C1s), and thymidine kinase 1 (TK1) genes in a blood sample from the subject to obtain a test expression profile, wherein assaying gene expression levels is performed using a method comprising at least one of: quantitative PCR, and a microarray;
   (b) comparing the test expression profile with a reference expression profile, wherein the reference expression profile comprises gene expression levels of CCL20, C1s, and TK1 that are indicative of either: (i) a renal graft tolerant phenotype; or (ii) a renal graft intolerant phenotype; and
   (c) detecting gene expression levels of CCL20, C1s, and TK1 in the test expression profile that are the same as the gene expression levels of CCL20, C1s, and TK1 in the reference expression profile that is indicative of a renal graft tolerant phenotype and determining that the human subject has a renal graft tolerant phenotype; or detecting gene expression levels of CCL20, C1s, and TK1 in the test expression profile that are increased compared to the gene expression levels of CCL20, C1s, and TK1 in the reference expression profile that is indicative of a renal graft intolerant phenotype and determining that the human subject has a renal graft tolerant phenotype.

2. The method according to claim 1, wherein the blood sample is a peripheral blood sample.

3. The method according to claim 1, wherein the step of assaying gene expression levels is performed using a method comprising quantitative PCR.

4. The method according to claim 1, wherein said assaying comprises assaying gene expression levels of at least one of: ecotropic viral integration site 2A (EVI2A) and mitogen-activated protein kinase 9 (MAPK9).

5. The method according to claim 1, wherein said assaying comprises assaying gene expression levels of at least one of: insulin-like growth factor binding protein 3 (IGFBP3), interleukin 13 receptor alpha 2 (IL13RA2), mitogen-activated protein kinase 9 (MAPK9), ecotropic viral integration site 2A (EVI2A), cadherin 2 (CDH2), parvin gamma (PARVG), and leukotriene B4 12-hydroxydehydrogenase (LTB4DH).

6. The method according to claim 5, wherein said assaying further comprises assaying gene expression levels of at least one of: alpha-fetoprotein (AFP), aldo-keto reductase family 1 member C1 (AKR1C1), barren homolog 1 (BRRN1), budding uninhibited by benzimidazoles 1 (BUB1), cell division cycle 2 (CDC2), CHK1 checkpoint homolog (CHEK1), melanoma associated gene (D2S448), dehydrogenase/reductase (DHRS2), nuclear receptor subfamily 2 group F member 1 (NR2F1), perkinje cell protein 4 (PCP4), podocalyxin-like (PODXL), RNA binding motif protein 9 (RBM9), regucalcin (RGN), serine protease inhibitor 3 (SERPINA3), serine protease inhibitor 5 (SERPINA5), SDR (sex determining region Y) box 3 (SOX3), spondin 1 (SPON1), and serine/threonine kinase 6 (STK6).

7. The method according to claim 1, wherein the step of assaying gene expression levels is performed using a method comprising a microarray.

8. A method for detecting a graft intolerant phenotype in a human subject, said method comprising:
   (a) assaying gene expression levels of chemokine (C-C motif) ligand 20 (CCL20), complement component 1s (C1s), and thymidine kinase 1 (TK1) genes in a blood sample from the subject to obtain a test expression profile, wherein assaying gene expression levels is performed using a method comprising at least one of: quantitative PCR, and a microarray;
   (b) comparing the test expression profile with a reference expression profile, wherein the reference expression profile comprises gene expression levels of CCL20, C1s, and TK1 that are indicative of either: (i) a renal graft tolerant phenotype; or (ii) a renal graft intolerant phenotype; and
   (c) detecting gene expression levels of CCL20, C1s, and TK1 in the test expression profile that are the same as the gene expression levels of CCL20, C1s, and TK1 in the reference expression profile that is indicative of a renal graft intolerant phenotype and determining that the human subject has a renal graft intolerant phenotype; or detecting gene expression levels of CCL20, C1s, and TK1 in the test expression profile that are decreased compared to the gene expression levels of CCL20, C1s, and TK1 in the reference expression profile that is indicative of a renal graft tolerant phenotype, and determining that the human subject has a renal graft intolerant phenotype.

9. The method according to claim 8, wherein the blood sample is a peripheral blood sample.

10. The method according to claim 8, wherein the step of assaying gene expression levels is performed using a method comprising quantitative PCR.

11. The method according to claim 8, wherein the step of assaying gene expression levels is performed using a method comprising a microarray.

12. The method according to claim 1, wherein the step of assaying gene expression levels comprises employing a fluorescently labeled probe or primer.

* * * * *

UNITED STATES PATENT AND TRADEMARK OFFICE
CERTIFICATE OF CORRECTION

PATENT NO. : 8,932,808 B1  
APPLICATION NO. : 10/585610  
DATED : January 13, 2015  
INVENTOR(S) : Minnie M. Sarwal Page 1 of 1

It is certified that error appears in the above-identified patent and that said Letters Patent is hereby corrected as shown below:

Title Page

Please replace

(73) Assignee: The Board of Trustees of the Leland Stanford Junior University, Palo Alto, CA (US)

with

(73) Assignees: The Board of Trustees of the Leland Stanford Junior University, Palo Alto, CA (US); INSERM, Paris (FR)

Signed and Sealed this  
Twelfth Day of January, 2016

Michelle K. Lee  
*Director of the United States Patent and Trademark Office*

```
                        SEQUENCE LISTING

<160> NUMBER OF SEQ ID NOS: 13

<210> SEQ ID NO 1
<211> LENGTH: 25
<212> TYPE: DNA
<213> ORGANISM: human

<400> SEQUENCE: 1
tcgcctttgc cgatccgccg cccgt                                         25

<210> SEQ ID NO 2
<211> LENGTH: 25
<212> TYPE: DNA
<213> ORGANISM: human

<400> SEQUENCE: 2
acacatgacc ggaacaccat ggagg                                         25

<210> SEQ ID NO 3
<211> LENGTH: 25
<212> TYPE: DNA
<213> ORGANISM: human

<400> SEQUENCE: 3
ttgccacaga cataaatgaa tgcac                                         25

<210> SEQ ID NO 4
<211> LENGTH: 25
<212> TYPE: DNA
<213> ORGANISM: human

<400> SEQUENCE: 4
aagcattttg taagattgcc aagta                                         25

<210> SEQ ID NO 5
<211> LENGTH: 25
<212> TYPE: DNA
<213> ORGANISM: human

<400> SEQUENCE: 5
gcagggcggc ggtcacagct acttc                                         25

<210> SEQ ID NO 6
<211> LENGTH: 25
```

-continued

```
<212> TYPE: DNA
<213> ORGANISM: human

<400> SEQUENCE: 6
gattgtttgt gctgcatttg ataca                                 25

<210> SEQ ID NO 7
<211> LENGTH: 25
<212> TYPE: DNA
<213> ORGANISM: human

<400> SEQUENCE: 7
agacattctt gcggagactg gggtt                                 25

<210> SEQ ID NO 8
<211> LENGTH: 25
<212> TYPE: DNA
<213> ORGANISM: human

<400> SEQUENCE: 8
caaggccgag ataggccagg ccatc                                 25

<210> SEQ ID NO 9
<211> LENGTH: 25
<212> TYPE: DNA
<213> ORGANISM: human

<400> SEQUENCE: 9
cgtttgtggg gttccattca gagcc                                 25

<210> SEQ ID NO 10
<211> LENGTH: 25
<212> TYPE: DNA
<213> ORGANISM: human

<400> SEQUENCE: 10
gatcaacggc tcccctgcc agcac                                  25

<210> SEQ ID NO 11
<211> LENGTH: 25
<212> TYPE: DNA
<213> ORGANISM: human

<400> SEQUENCE: 11
ctgcagagct cagtcagagg gcaga                                 25

<210> SEQ ID NO 12
<211> LENGTH: 25
<212> TYPE: DNA
<213> ORGANISM: human

<400> SEQUENCE: 12
ggtcaaggtc gcaagcttgc tggtg                                 25

<210> SEQ ID NO 13
<211> LENGTH: 25
<212> TYPE: DNA
<213> ORGANISM: human

<400> SEQUENCE: 13
gggcgcctgg tcaccagggc tgctt                                 25
```